United States Patent
Rhee et al.

(10) Patent No.: US 9,898,120 B2
(45) Date of Patent: Feb. 20, 2018

(54) WATCH TYPE MOBILE TERMINAL AND CONTROL METHOD FOR THE MOBILE TERMINAL

(71) Applicant: LG ELECTRONICS INC., Seoul (KR)

(72) Inventors: Jeongyoon Rhee, Seoul (KR); Taeseong Kim, Seoul (KR); Yujune Jang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/699,282

(22) Filed: Apr. 29, 2015

(65) Prior Publication Data

US 2015/0338979 A1 Nov. 26, 2015

(30) Foreign Application Priority Data

May 23, 2014 (KR) ........................ 10-2014-0062479

(51) Int. Cl.
*G06F 3/041* (2006.01)
*G06F 3/048* (2013.01)
*G06F 1/16* (2006.01)
*G06F 3/01* (2006.01)
*G06F 21/31* (2013.01)
(Continued)

(52) U.S. Cl.
CPC ............ *G06F 3/0414* (2013.01); *A61B 5/681* (2013.01); *G06F 1/163* (2013.01); *G06F 3/014* (2013.01); *G06F 3/017* (2013.01); *G06F 3/0488* (2013.01); *G06F 21/31* (2013.01)

(58) Field of Classification Search
None
See application file for complete search history.

(56) References Cited

U.S. PATENT DOCUMENTS

2008/0244699 A1* 10/2008 Parhofer ............... F41A 17/063
726/2
2009/0146947 A1 6/2009 Ng
2010/0219943 A1 9/2010 Vanska et al.
(Continued)

FOREIGN PATENT DOCUMENTS

EP 1 291 748 A2 3/2003
EP 2 378 748 A1 10/2011
(Continued)

OTHER PUBLICATIONS

Huang, Wei Min, "Shape Memory Polymers (SMPs)—Current Research and Future Applications," May 25, 2012, AZO Materials, pp. 1-14.*

(Continued)

*Primary Examiner* — Patrick Edouard
*Assistant Examiner* — Maheen Javed
(74) *Attorney, Agent, or Firm* — KED & Associates, LLP

(57) ABSTRACT

Disclosed is a watch type mobile terminal wearable on a wrist. The watch type mobile terminal includes a main body, a band unit, a sensing unit and a controller. The main body has a display unit. The band unit is connected to the main body so that the mobile terminal is worn on the wrist, and surrounds the wrist. The sensing unit senses at least one tap applied to at least one of the main body and the band unit. The controller configured performs a function corresponding to a pattern to which the tap is applied.

14 Claims, 26 Drawing Sheets

(51) Int. Cl.
*A61B 5/00* (2006.01)
*G06F 3/0488* (2013.01)

(56) References Cited

U.S. PATENT DOCUMENTS

| | | | | |
|---|---|---|---|---|
| 2013/0131887 | A1* | 5/2013 | Park | G05B 11/01 |
| | | | | 700/303 |
| 2013/0245390 | A1 | 9/2013 | Hyde et al. | |
| 2013/0261405 | A1* | 10/2013 | Lee | A61B 5/681 |
| | | | | 600/301 |
| 2014/0062892 | A1* | 3/2014 | Dickinson | G06F 3/0412 |
| | | | | 345/173 |
| 2014/0139637 | A1* | 5/2014 | Mistry | H04N 5/2252 |
| | | | | 348/46 |
| 2014/0295918 | A1* | 10/2014 | Grifoni | H04M 1/7253 |
| | | | | 455/566 |
| 2014/0310643 | A1* | 10/2014 | Karmanenko | G06F 1/1626 |
| | | | | 715/784 |
| 2015/0091711 | A1* | 4/2015 | Kosonen | G08B 6/00 |
| | | | | 340/407.1 |
| 2017/0098435 | A1* | 4/2017 | Inagaki | G09G 5/37 |

FOREIGN PATENT DOCUMENTS

| | | | |
|---|---|---|---|
| EP | 2 733 579 A2 | 5/2014 | |
| EP | 2 733 594 A1 | 5/2014 | |
| EP | 3 015 948 | 5/2016 | |
| EP | 3 046 000 | 7/2016 | |
| GB | 2508016 A * | 5/2014 | ........... G06F 21/629 |
| JP | 2007-125246 | 5/2007 | |
| WO | WO 2014/035680 | 3/2014 | |
| WO | WO 2014/035680 A2 | 3/2014 | |
| WO | WO 2014/200988 A1 | 12/2014 | |
| WO | WO 2016/019002 | 2/2016 | |

OTHER PUBLICATIONS

European Search Report dated Mar. 10, 2016 issued in Application No. 15001271.4.
European Search Report issued in Application No. 15001271.4 dated Oct. 21, 2015.
LG: "LG G2 User Guide," Apr. 24, 2014, XP055217541, Retrieved from the Internet: URL: http://www.lg.com/uk/support/software-manuals#.
European Search Report dated Oct. 5, 2017 issued in Application No. 17000848.6.

* cited by examiner (A)

(B)

WATCH TYPE MOBILE TERMINAL AND CONTROL METHOD FOR THE MOBILE TERMINAL

CROSS-REFERENCE TO RELATED APPLICATION

Pursuant to 35 U.S.C. § 119(a), this application claims the benefit of earlier filing date and right of priority to Korean Application No. 10-2014-0062479, filed on May 23, 2014, the contents of which is incorporated by reference herein in its entirety.

BACKGROUND OF THE INVENTION

1. Field of the Invention

The present disclosure relates to a watch type mobile terminal wearable on a wrist.

2. Description of the Conventional Art

In general, a terminal may be classified into a mobile (portable) terminal and a stationary terminal according to a moveable state. The mobile terminal may be also classified into a handheld terminal and a vehicle mount terminal according to a user's carriage method.

As functions of the terminal become more diversified, the terminal can support more complicated functions such as capturing images or video, reproducing music or video files, playing games and receiving broadcast signals. By comprehensively and collectively implementing such functions, the mobile terminal may be embodied in the form of a multimedia player or a device. Various attempts have been made to implement complicated functions in such a multimedia device by means of hardware or software. For instance, a user interface (UI), which allows a user to search for or select functions in an easy and convenient manner, is provided.

As the mobile terminal is regarded as a personal belonging for expressing the user's own personality, various design shapes of the mobile terminal are required. The design shapes also includes structural changes and improvements which enable the user to more conveniently use the mobile terminal. A watch type mobile terminal that can be used while being worn on a user's wrist may be considered as one of the structural changes and improvements.

SUMMARY OF THE INVENTION

Therefore, an aspect of the detailed description is to provide a watch type mobile terminal in which new user inputs and new outputs of the terminal are possible.

Another aspect of the detailed description is to provide a watch type mobile terminal in which a plurality of input forms can be defined using a band unit.

Still another aspect of the detailed description is to provide a control method for controlling a watch type mobile terminal, using a band unit.

Still another aspect of the detailed description is to provide a control method for simultaneously controlling a watch type mobile terminal and another terminal linked with the watch type mobile terminal, using a band unit.

To achieve these and other advantages and in accordance with the purpose of this specification, as embodied and broadly described herein, a watch type mobile terminal wearable on a wrist includes: a main body configured to have a display unit; a band unit connected to the main body so that the mobile terminal is worn on the wrist, the band unit surrounding the wrist; a sensing unit configured to sense at least one tap applied to at least one of the main body and the band unit; and a controller configured to perform a function corresponding to a pattern to which the tap is applied.

In one exemplary embodiment, the pattern may be defined by positions at which the plurality of taps are respectively applied on the main body and the band unit and an order in which the plurality of taps are applied at the positions.

In one exemplary embodiment, the main body and the band unit may be divided into a plurality of areas. The pattern may be defined by an order in which at least one of the plurality of areas is selected by the plurality of taps.

In one exemplary embodiment, if the number of touch points included in one tap applied to the at least one area is different from that of touch points included in another tap applied to the at least one area, the controller may recognize the taps as different patterns.

In one exemplary embodiment, the mobile terminal may further include a memory configured to include matching information in which different functions are respectively matched to a plurality of patterns. The controller may perform a function matched to a pattern to which the plurality of taps are applied among the plurality of patterns. One of the matched functions may be a function of switching, to a release state, a locking state in which a user's input with respect to the mobile terminal is limited.

In one exemplary embodiment, when a plurality of taps are applied in an order opposite to that in which the plurality of taps forming a pattern matched to the release state are applied after the locking state is released, the controller may switch the release state to the locking state.

In one exemplary embodiment, if a plurality of taps corresponding to the pattern matched to the function of switching the locking state to the release state of the terminal are applied, the controller may switch the state of the mobile terminal to the release state. The controller may determine a function to be performed after the state of the mobile terminal is switched to the release state, based on a kind of the pattern formed by the plurality of taps.

In one exemplary embodiment, a terminal of which locking state is to be switched to the release state may be determined based on the number of touch points included in the plurality of taps.

In one exemplary embodiment, if a release pattern matched to the function of switching the locking state to the release state is made through a plurality of taps including one touch point, the controller may control the locking state of the mobile terminal. If the release pattern is made through a plurality of taps including two touch points, the controller may control the locking state of the mobile terminal and the locking state of at least one another terminal paired with the mobile terminal.

In one exemplary embodiment, if the release pattern is made through a plurality of taps including two touch points, the controller may transmit, to the at least one another terminal, a control signal corresponding to a locking release command.

In one exemplary embodiment, when the plurality of taps applied to the band unit do not form the pattern, the controller may execute a guest mode in which a user's access to some functions of the mobile terminal is limited.

In one exemplary embodiment, the positions, order and number of times, where the plurality of taps forming the pattern are applied, may be determined by a user's selection.

In one exemplary embodiment, the band unit may include first and second bands respectively connected to both sides of the main body, the first and second bands being fastened to each other. When the plurality of taps forming the pattern are applied in a state in which the first and second bands are fastened to each other, the controller may perform a function corresponding to the pattern.

In one exemplary embodiment, the function being performed in the state in which the first and second bands are fastened to each other may be stopped when the fastening between the first and second bands is released.

In one exemplary embodiment, when the function corresponding to the pattern is a locking release function of switching a locking state to a release state of the mobile terminal, the release state may be again switched to the locking state, based on that the fastening between the first and second bands is released.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF EXEMPLARY EMBODIMENTS

Description will now be given in detail of the exemplary embodiments, with reference to the accompanying drawings. For the sake of brief description with reference to the drawings, the same or equivalent components will be provided with the same reference numbers, and description thereof will not be repeated. A suffix "module" or "unit" used for constituent elements disclosed in the following description is merely intended for easy description of the specification, and the suffix itself does not give any special meaning or function. In describing the present invention, if a detailed explanation for a related known function or construction is considered to unnecessarily divert the gist of the present disclosure, such explanation has been omitted but would be understood by those skilled in the art. The accompanying drawings are used to help easily understood the technical idea of the present invention and it should be understood that the idea of the present disclosure is not limited by the accompanying drawings.

A terminal in the present description may include a mobile terminal such as a portable phone, a smart phone, a notebook computer, a digital broadcasting terminal, Personal Digital Assistants (PDA), Portable Multimedia Player (PMP), a navigation system, a slate PC, a tablet PC, an ultra book, a wearable device (e.g., smart watch), a glass-type terminal (e.g., smart glass), a head mounted display (HMD), etc.

However, it will be obvious to those skilled in the art that the present invention may be also applicable to a fixed terminal such as a digital TV, a desktop computer and a digital signage, except for specific configurations for mobility.

Figure 1A:
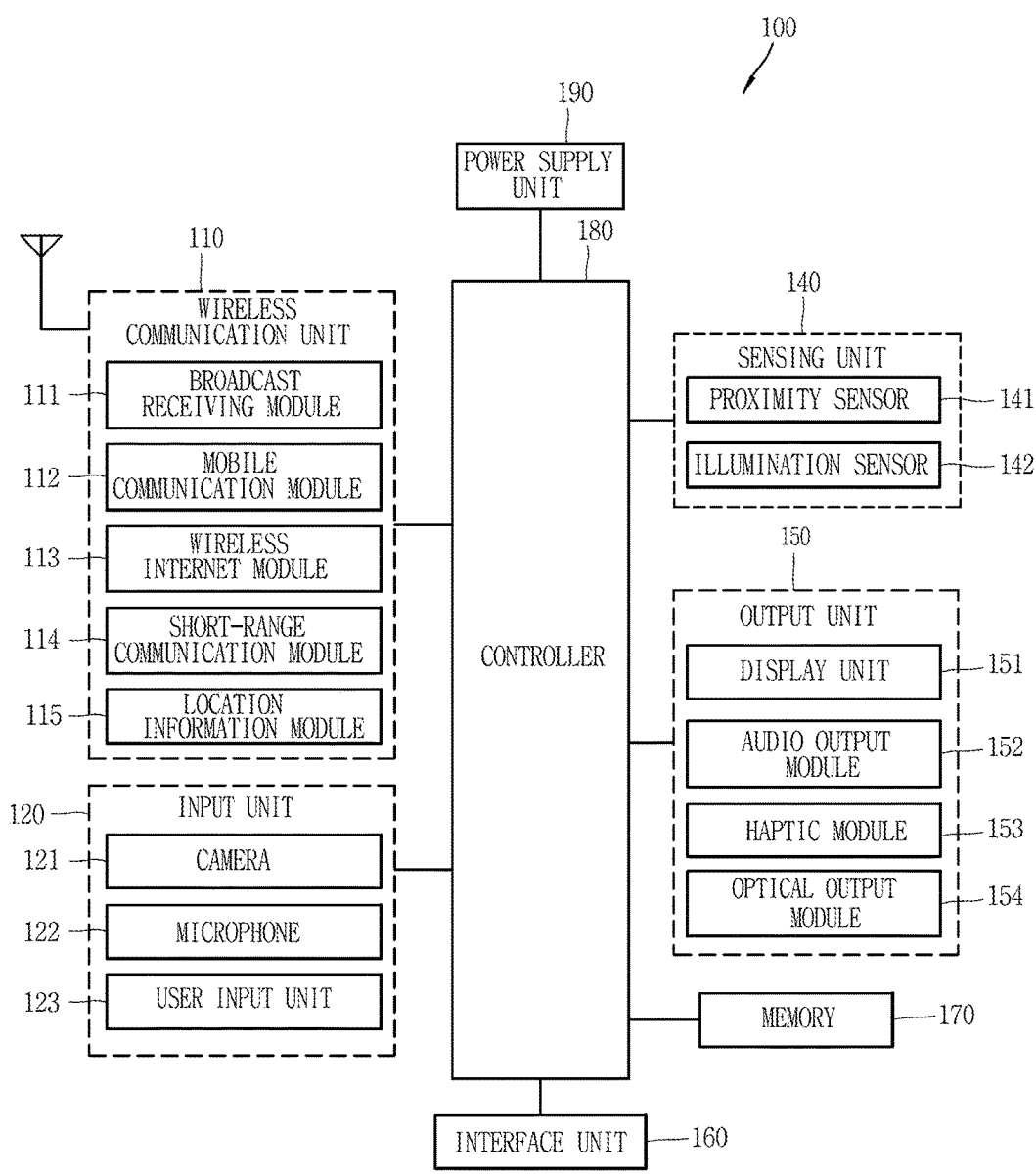
FIG. 1A is a block diagram illustrating a mobile terminal according to an exemplary embodiment.
Figure 1B:
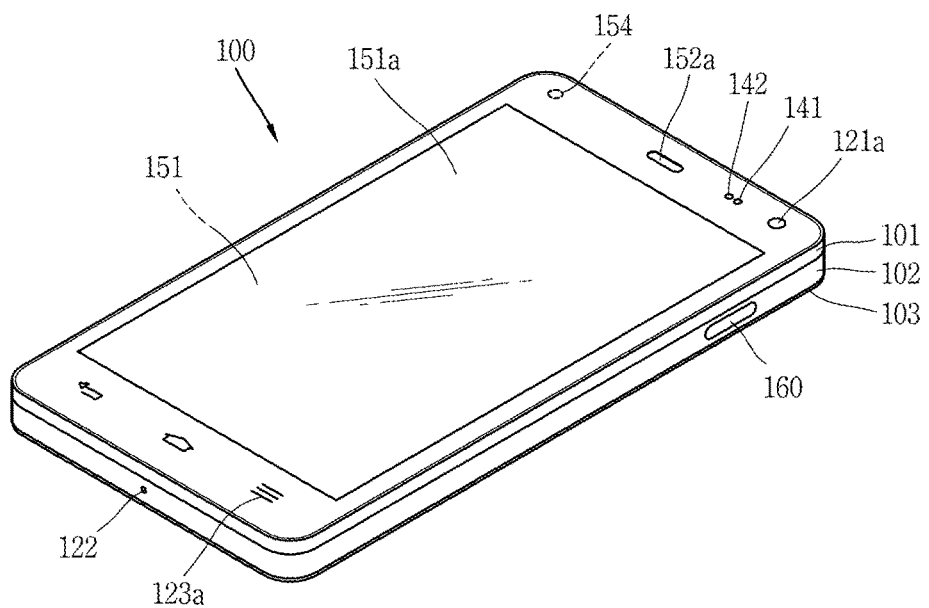
FIGS. 1B and 1C are conceptual diagrams illustrating an example of the mobile terminal viewed in different directions according to the exemplary embodiment.
Figure 1C:
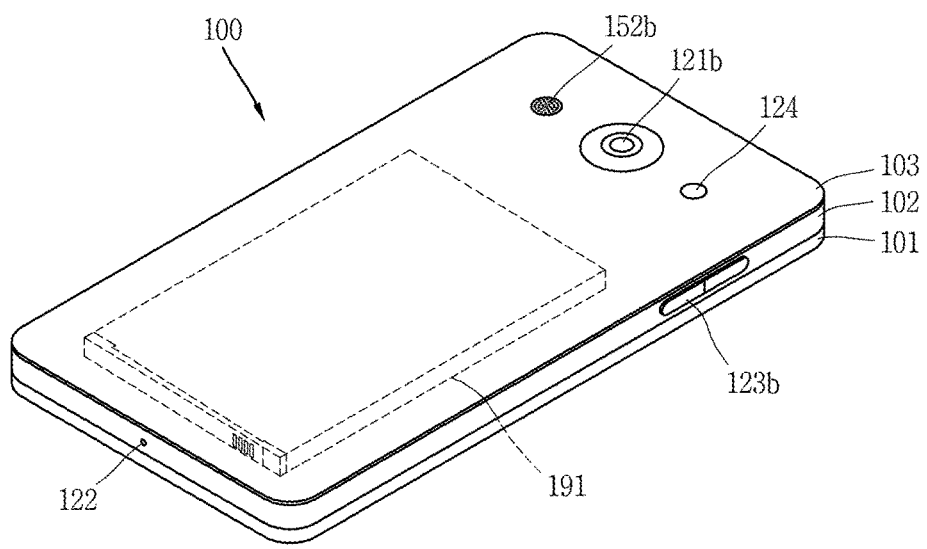

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components of FIG. 1A is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), Wideband CDMA (WCDMA), High Speed Downlink Packet access (HSDPA), Long Term Evolution (LTE), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, GSM, CDMA, WCDMA, LTE and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the mobile terminal. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The display unit 151, the first audio output module 152a, the second audio output module 152b, the proximity sensor 141, the illumination sensor 142, the optical output module 154, a first camera 121a, a second camera 121b, the first manipulation unit 123a, the second manipulation unit 123b, the microphone 122, the interface 160, etc. may be provided at the mobile terminal 100.

As shown in FIGS. 1B and 1C, the display unit 151, the first audio output module 152a, the proximity sensor 141, the illumination sensor 142, the optical output module 154, the first camera 121a and the first manipulation unit 123a are arranged on a front surface of the terminal body. The second manipulation unit 123b, the microphone 122 and the interface 160 are arranged on side surfaces of the terminal body. And the second audio output module 152b and the second camera 121b are arranged on a rear surface of the terminal body.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable mobile terminals. Examples of such suitable mobile terminals include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two mobile terminals, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a receiver, and the second audio output module 152b may be implemented in the form of a loud speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151 a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may be implemented in a user's non-tactile manner, e.g., by a proximity touch, a hovering touch, etc.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 (refer to FIG. 1A) may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 2:
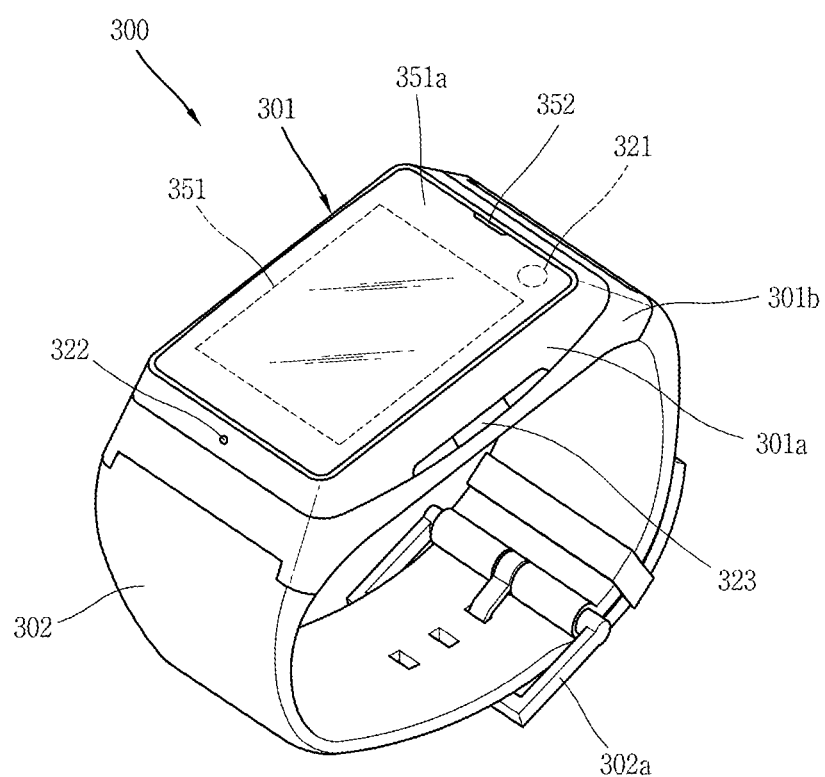
FIG. 2 is a perspective view illustrating an example of a watch type mobile terminal according to another exemplary embodiment.

FIG. 2 is a perspective view illustrating one example of a watch-type mobile terminal 300 in accordance with another exemplary embodiment. As illustrated in FIG. 2, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

Meanwhile, as described above, the controller 180 (see FIG. 1A) may control functions of the terminal using a band of the mobile terminal.

In the present disclosure, a method for defining a plurality of input forms and controlling operations of the display unit 351 using the input forms will be proposed as one of the control methods. Hereinafter, a method for controlling functions of the watch type mobile terminal using the band will be described in detail with reference to the accompanying drawings.

For convenience of illustration, hereinafter, the band will be divided into first and second bands connected to each other by a fastener 302a. In addition, the band 302 described with reference to FIG. 2 will be referred to as a band unit that includes the first and second bands. It should be appreciated, however, that the band or band unit may also be referred to as a band assembly, strap, watch strap, or the like. In the present disclosure, the first band is described using reference numeral "303", and the second band is described using reference numeral "304". Further, with respect to contents applicable to both the first and second bands without division into the first and second bands, the first and second bands will be described as the "band unit 302" instead of the reference numerals for representing the first and second bands.

Figure 3:
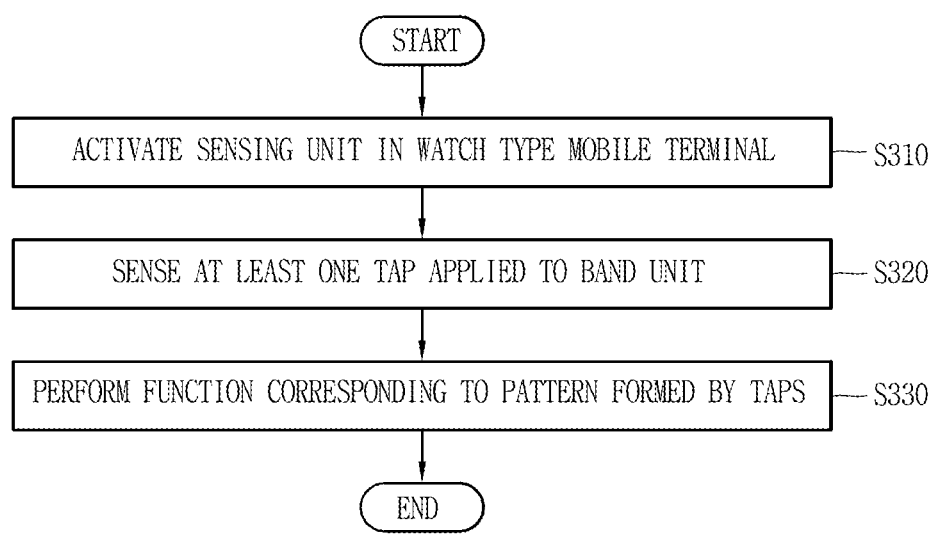
FIG. 3 is a flowchart representatively illustrating a control method according to an exemplary embodiment.

FIG. 3 is a flowchart representatively illustrating a control method according to an exemplary embodiment. FIGS. 4A to 4E are conceptual diagrams a band area applied to the control method described in FIG. 3.

Referring to FIG. 3, first, the sensing unit 140 (see FIG. 1A) of the watch type mobile terminal is activated (S310).

In this case, the sensing unit 140 is configured to receive a user input applied to the band unit, and the activation means that the sensing unit 140 is prepared in a ready state for receiving the user input.

The sensing unit 140 includes one or more sensors for sensing a user input applied to the band unit, and the sensor may be disposed in the band unit.

If the power of the terminal is on even when a sleep mode for allowing most components including the display unit 351 and the like to be non-activated in order to minimize battery consumption, the sensor disposed in the band unit may be activated to always sense the user input. That is, the sensor disposed in the band unit may be in a continuously activated (always-on) state while the power is being supplied to the controller.

Alternatively, other sensors except the sensor disposed in the band unit may be non-activated in the sleep mode. In this case, when a user input is sensed by the sensor disposed in the band unit, the other sensors may be activated.

The sensor disposed in the band unit may be activated only when a user input applied to another portion exists in the state in which the sensor is non-activated. As an example, if the terminal senses touch inputs (e.g., first and second tappings) consecutively applied to the display unit 351 at a time interval, the sensor disposed in the band unit may be activated. As another example, if a push input is applied to a separate physical key provided in the terminal, the sensor disposed in the band unit may be activated.

Next, the sensing unit senses a user input applied to the band unit (S320).

In the sensing (S320), the user input may be an input using a predetermined method, which is linked with a function of inputting a control command to the terminal.

Here, the sensing unit may sense at least one tap applied to the band unit. Here, the tap may be understood as an input corresponding to a touch input touching the band unit.

Further, the user input may be a physical input (a push input, a bend input, a flip input, or the like). To this end, the sensor disposed in the band unit may be configured to sense at least one of the touch input and the physical input, which are applied to the band unit. More specifically, the sensor may be a touch sensor for sensing the touch input or a resonant sensor. Alternatively, the sensor may be a dome switch or piezoelectric sensor for sensing the push input, or may be a bending sensor or hole sensor for sensing the bend input, flip input, or the like. Alternatively, two or more of the touch sensor, the dome switch, the piezoelectric sensor, the bending sensor and the hole sensor may be combined together, so that the sensing unit senses all the touch input, the push input, the bend input, the flip input, and the like.

However, the present disclosure is not necessarily limited thereto, and the touch input, the push input, the bend input and the flip input may be sensed by at least one of the proximity sensor 141, the illumination sensor 142, an acceleration sensor, a motion sensor, an RGB sensor, an infrared sensor (IR sensor), a finger scan sensor, an ultrasonic sensor and an optical sensor (e.g., the camera (see 121)).

Finally, the controller performs a function corresponding to a pattern formed by a plurality of taps applied to the band unit (S330).

Here, the pattern formed by the plurality of taps may be defined by positions at which the respective taps are applied on the band unit 302 and an order in which the plurality of taps are applied at the respective positions.

More specifically, the band unit 302 may be divided into a plurality of areas, and the pattern may be defined by an order in which at least one of the plurality of areas is selected by the plurality of taps.

Figure 4A:
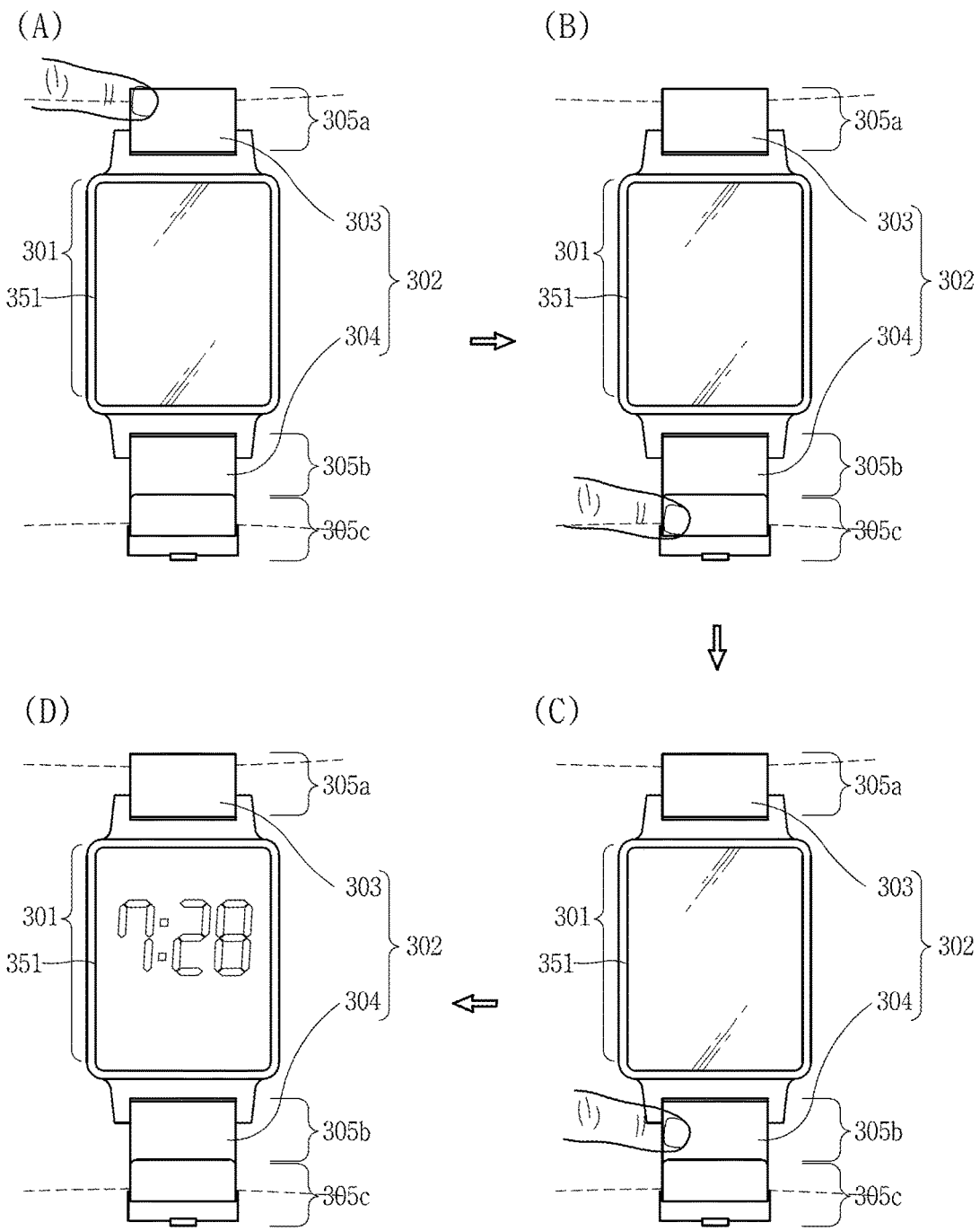
FIGS. 4A to 4E are conceptual diagrams of a band area applied to the control method described in FIG. 3.

For example, referring to FIG. 4A, the band unit 302 may be divided into three areas, i.e., a first area 305*a*, a second area 305*b* and a third area 305*c*. The pattern applied to the band unit may be defined based on an order in which at least one of the first, second and third areas 305*a*, 305*b* and 305*c* is selected by the taps applied to the band unit 302.

For example, a function of switching a locking state (e.g., locked) to a release state (e.g., unlocked) of the terminal may be performed by a plurality taps applied to the band unit 302. When the function of switching the locking state to the release state of the terminal is previously defined to be performed when the first area 305*a*, the third area 305*c* and the second area 305*b* are sequentially selected by taps as shown in FIG. 4A (a), (b) and (c), the controller switches the locking state to the release state only when the first area 305*a*, the third area 305*c* and the second area 305*b* are sequentially selected in the locking state.

For example, when the first area 305*a*, the second area 305*b* and the third area 305*c* are sequentially selected, the controller may continuously maintain the locking state.

Here, the locking state means a state in which the reception of a control command input by a user is limited. The locking state refers to a state in which locking is released only when a password set by a specific person is necessarily input. When the display unit 351 is activated in the locking state, a locking screen for requiring a password to be input or requiring an additional user input in order to release the locking state may be displayed on the display unit 351.

Meanwhile, in the present disclosure, the locking state is released based on a release command defined in a pattern formed by a plurality of taps of tapping the terminal in a state the display unit 351 is non-activated, and therefore, it may not be required to output a separate screen for releasing the locking state. Thus, the user can release the locking of the terminal without inputting a password to the display unit on which the locking screen is displayed.

Meanwhile, pattern information on a plurality of patterns and matching information to which different functions are matched may be stored in the memory 170.

For example, when the pattern formed by a plurality of taps applied to the band unit 302 is a first pattern, the controller may perform a first function matched to the first pattern. When the pattern formed by the plurality of taps is a second pattern different from the first pattern, the controller may perform a second function matched to the second pattern.

That is, the controller may perform different functions based on patterns formed by a plurality of taps applied to the band unit 302.

As such, the controller performs functions matched to patterns formed by the plurality of taps. As described above, one of the matched functions may be a function of switching the locking state in which the user input with respect to the terminal is limited to the release state.

Further, the pattern for switching the locking state to the release state may exist in plural numbers. Functions to release the locking state and be performed may be respectively linked with the plurality of patterns. For example, if a first pattern in applied, the controller may release the locking state and perform a first function. If a second pattern different from the first pattern is applied, the controller may release the locking state and perform a second function different from the first function. Here, the first function may be a function of executing a specific application, and the second function may be a function of outputting a home screen page output in the watch type mobile terminal.

Meanwhile, if the number of touch points included in one tap is different from that of touch points included in another tap, the controller may decide the taps as different patterns. For example, when the band unit is tapped with one finger and when the band unit is tapped with two fingers, the controller may recognize the two cases as different patterns. Thus, if the number of touch points included in one tap is different from that of touch points included in another tap with respect to a plurality of areas even though the plurality of areas are tapped in the same order, the controller recognizes the taps as different input.

Meanwhile, when a plurality of taps applied to the band unit do not form a predetermined pattern, the controller may not perform control processing on the plurality of taps. That is, when the plurality of taps do not form the predetermined pattern, the controller may neglect the plurality of taps. In this state, when the display unit 351 is in a non-activated state, the controller may continuously maintain the non-activated state of the display unit 351. Here, the "non-activated state of the display unit 351" means that illumination provided inside the display unit 351 to illuminate the display unit 351 is in an off state. In the state in which the display unit 351 is non-activated, any information or graphic image is not displayed on the display unit 151. Meanwhile, the "activated state of the display unit 151" means that the illumination provided inside the display unit 351 to illuminate the display unit 351 is in an on state.

Alternatively, when the plurality of taps applied to the band unit do not form the predetermined pattern, the controller may execute a guest mode in which the user's access to some functions of the terminal is limited. In this case, the terminal may allow the user to have access to only some functions. The kind of a function or application accessible in the guest mode may be determined based on a user's selection.

Here, the some functions to which the access is limited may be functions related to user's privacy.

Meanwhile, although the case where the taps constituting the pattern are applied to the band unit 302 has been described in the above, the present invention is not limited thereto. As an example, at least one of the taps constituting the pattern, as shown in FIG. 4A, may be applied to the main body 301 or the display unit 351. That is, the main body 301 or the display unit 351 may become one additional area except a plurality of areas formed on the band unit. In this case, the controller may sense taps applied to at least one of the band unit and the main body (or the display unit). The controller may perform a function corresponding to a pattern formed by the sensed taps, using the taps sensed in the band unit and the main body (or the display unit).

Meanwhile, taps applied to the band unit will be mainly illustrated in the following description, but it will be apparent that the taps may also be applied to the main body (or the display unit). That is, the area to which the taps can be applied may be configured to include the main body (or the display unit).

Figure 4B:
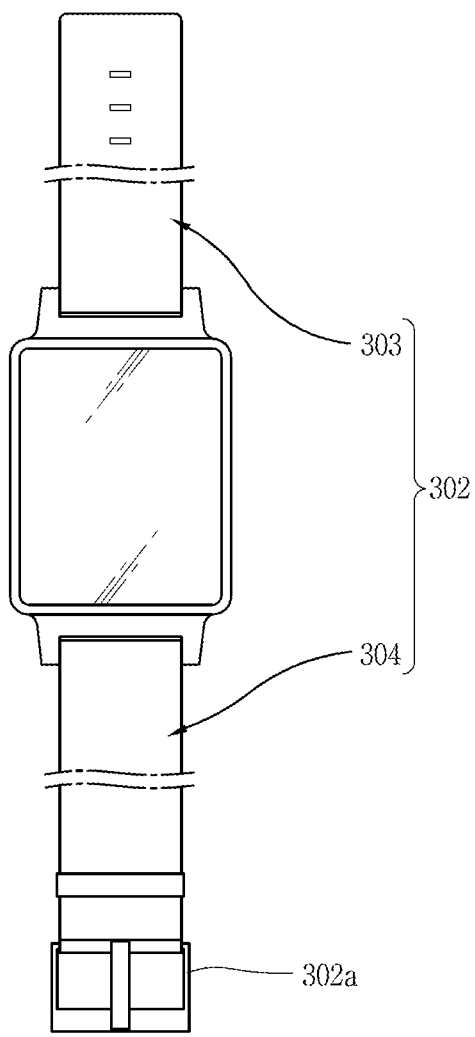
Figure 4C:
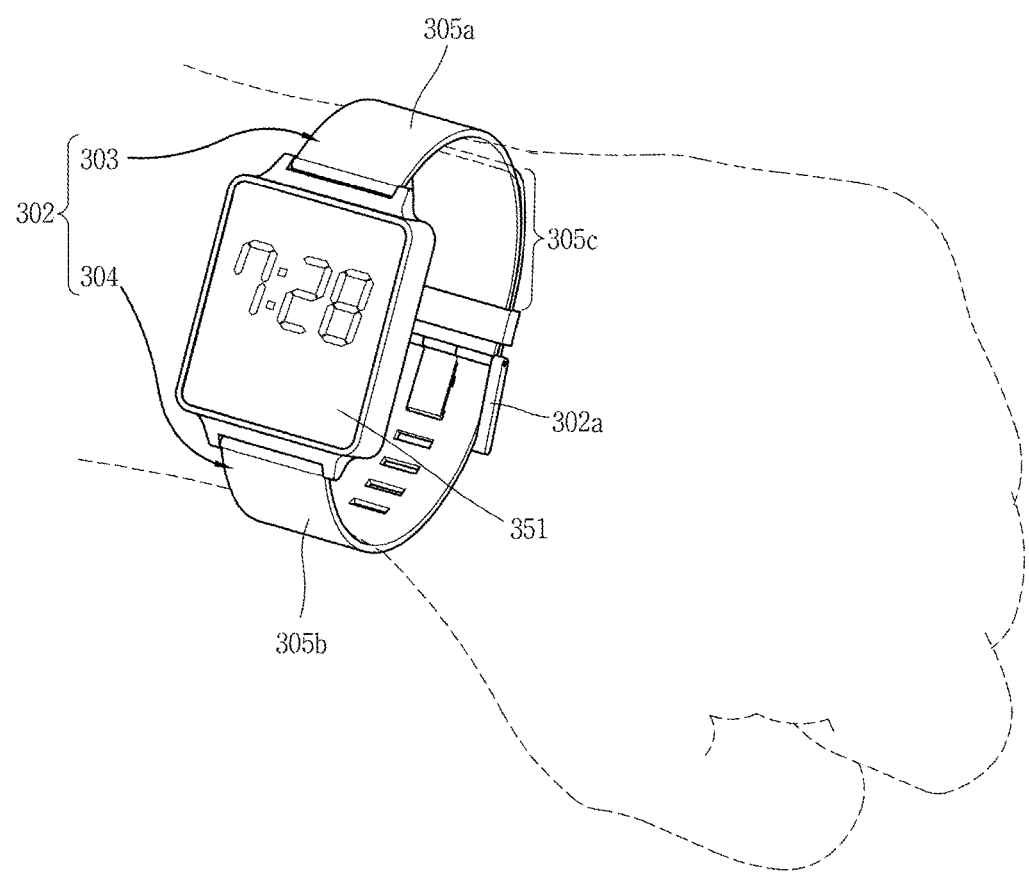

Hereinafter, a plurality of areas into which the band unit 302 is divided will be described in detail. Referring to FIGS. 4B and 4C, the band unit has a plurality of areas for sensing the user's input. At least one of the sensors described above may be provided in the plurality of areas. In this case, the controller may detect a control command applied to at least one of the plurality of areas, using information sensed in any one of the sensors, or may recognize a control command applied to at least one of the plurality of areas by combining information sensed in two or more sensors.

The band unit 302 includes first and second bands 303 and 304 respectively connected to both sides of the main body, and the plurality of areas are defined by fastening between the first and second bands 303 and 304. The first band 303 is connected to one end (top end) of the main body, and the second band 304 is connected to the other end (bottom end) of the main body. The first and second bands 303 and 304 are fastened to each other by a fastener 302a (see FIG. 2) so that the terminal is worn on a wrist. When the terminal is not worn, the first and second bands 303 and 304 may be separated from each other. However, the present invention is not necessarily limited thereto. Functions described below may be applied even when the first band is connected to the bottom end and the second band is connected to the top end.

As shown in these figures, the plurality of areas include a first area 305a, a second area 305b and a third area 305c. The first area 305a may be formed in the first band 303, and the second area 305b may be formed in the second band 304. The third area 305c may be an area in which the first and second bands 303 and 304 are overlapped with each other. More specifically, the first area 305a may be an area except the third area 305c in the first band 303, and the second area 305b may be an area except the third area 305c in the second band 304. The band unit may be formed so that the length of the band unit can be adjusted when the terminal is worn on the wrist.

However, the present invention is not necessarily limited thereto, and the third area may be defined as, for example, an area in which the first and second bands 303 and 304 are connected to each other. For example, unlike as shown in these figures, the third area may be an area for connecting the first and second bands 303 and 304 so that the first and second bands 303 and 304 are engaged with each other.

A double band unit may be formed by the overlapping or connection of the first and second bands 303 and 304, and the sensing unit may be configured to sense a user input applied to the double band unit.

Hereinafter, the third area illustrates only the area in which the first and second bands 303 and 304 are overlapped with each other. However, in exemplary embodiments described below, the third area may be the area in which the first and second bands 303 and 304 are connected to each other (or the area for connecting the first and second bands 303 and 304 so that the first and second bands 303 and 304 are engaged with each other) or the double band unit.

In this case, the sizes of the first, second and third areas 305a, 305b and 305c may be changed by the adjustment of the length. The sizes (or widths) of the first, second and third areas 305a, 305b and 305c may be changed corresponding to the adjustment of the length.

As such, the plurality of areas may be divided by the fastening between the first and second bands 303 and 304, and the pattern that a plurality of taps form based on the user input may be formed by at least one of the order and number of times, where the plurality of areas are selected by the plurality of taps.

Figure 4D:
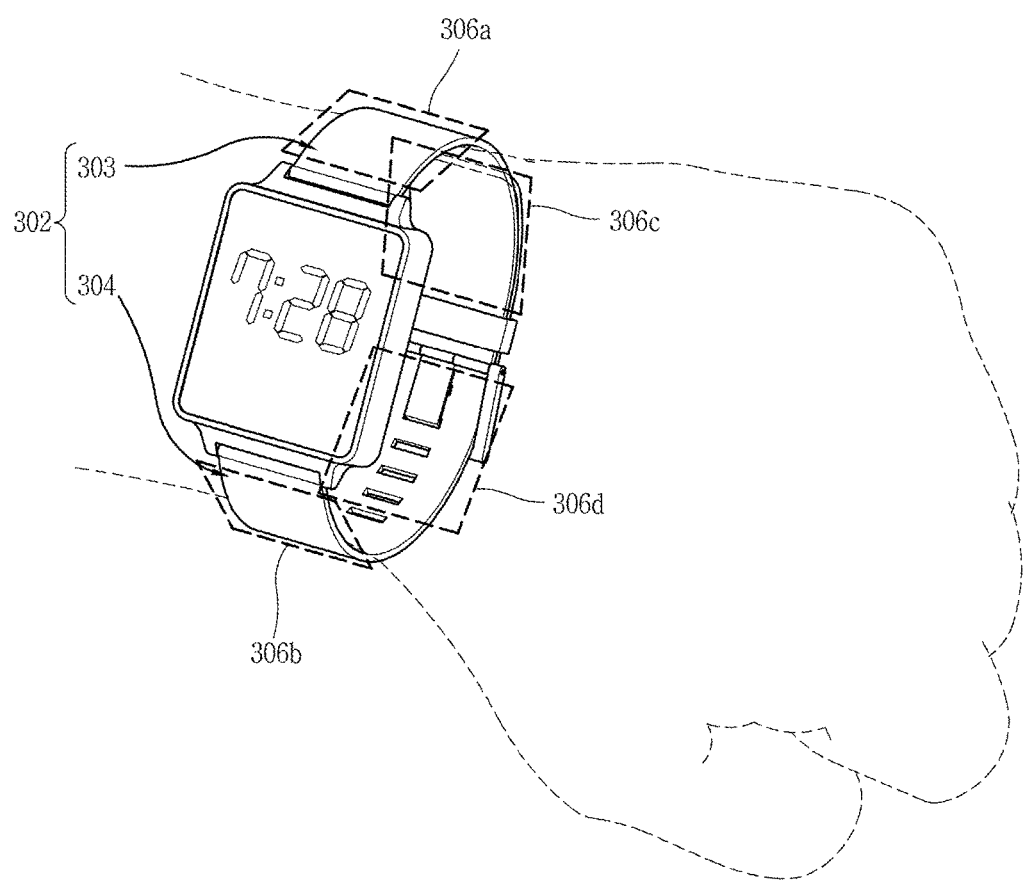

As another example, the band unit 302, as shown in FIG. 4D, may be divided into N equal parts in the state in which the first and second bands 303 and 304 are fastened, to be divided into a plurality of areas. Here, which equal part the band unit is to be divided into may be determined by a user's selection, or may be previously determined through programming when the terminal is manufactured. As shown in this figure, the band unit 302 may be divided into first, second, third and fourth areas 306a, 306b, 306c and 306d.

Meanwhile, as described above, the plurality of areas included in the band unit 302 may be respectively matched to different numerals. For example, as described in FIGS. 4B and 4C, the first, second and third areas 305a, 305b and 305c may be respectively matched to numerals '1', '2' and '3'.

Thus, the user sets a password or pattern using 'numbers' on the terminal and then sequentially taps areas respectively corresponding to the numbers that correspond to the set password or pattern, thereby forming the pattern.

For example, as shown in FIG. 4A, when numerals called '132' are set to a password for switching the locking state to the release state, the controller 180 may switch the locking state to the release state when the first, third and second areas 305a, 305c and 305b are sequentially tapped.

Meanwhile, the number of numerals assigned to each area may be changed based on the number of divided areas. For example, as shown in FIG. 4D, when the band unit is divided into four areas, four numerals may be matched to the respective areas.

The number of divided areas may be changed based on the length of numerals forming a password or pattern. For example, when a password is set within numerals of 1 to 5, the band unit may be divided into five areas.

As such, the number of numerals assigned to may be determined based on the number of the divided areas. On the contrary, the number of the divided areas may be changed depending on the length of numerals set to the password.

Further, in the present disclosure, when the main body 301 is assigned as another area that can be tapped, one numeral may be assigned to the main body 301. For example, in FIG. 4A, numerals may be respectively assigned to the first area 305a, the second area 305b, the third area 305c and the main body 301. In this case, the user may set a password or the like, using four numerals different from one another.

In the exemplary embodiment described above, a pattern formed by taps with respect to the band unit 302 has been described. However, the pattern may be formed by combining taps with respect to the band unit 302 and taps applied to another component such as the main body (including the display unit 351) of the watch type mobile terminal.

Meanwhile, in the present disclosure, when a plurality of taps forming a predetermined pattern are applied in an order opposite to that in which the plurality of taps are applied to form the predetermined pattern, the controller may perform another function linked with a function matched to the predetermined pattern. For example, when the function matched to the predetermined pattern is a function of executing a specific application, the controller may finish the specific application when the taps forming the predetermined pattern are applied in the opposite order.

Figure 4E:
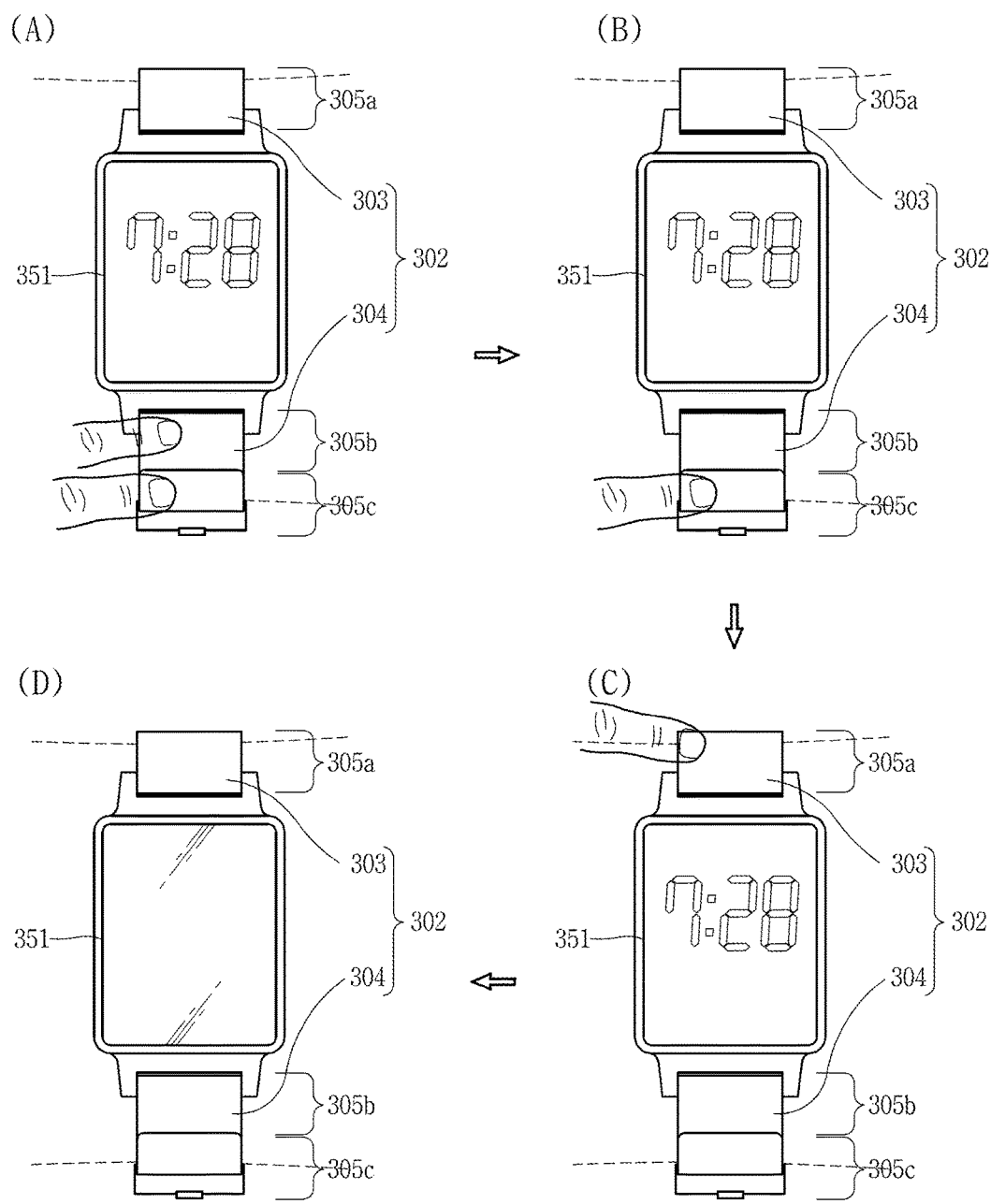

More specifically, as shown in FIG. 4E (a), (b) and (c), when the plurality of taps are applied in an order opposite to that in which the taps forming matched to the function of switching the locking state to the release state are applied as shown in FIG. 4A (a), (b) and (c), the controller may again switch the release state to the locking state as shown in FIG. 4E (d).

As such, after the locking state is released, the controller may switch the release state to the locking state when a plurality of taps forming a pattern matched to the release state are applied in an order opposite to that in which the plurality of taps are applied.

As described above, in the present disclosure, an input is applied to the watch type mobile terminal using the band unit in order to provide new user convenience. Further, as the band unit is divided into a plurality of areas, various forms of control methods can be implemented.

Hereinafter, a method for controlling another communicating with the watch type mobile terminal, using a user input with respect to the band unit, will be described in detail with reference to the accompanying drawings. FIGS. 5A, 5B, 6A, 6B and 7 are conceptual diagrams illustrating a representative exemplary embodiment in which the mobile terminal is controlled using a user input applied to the band unit.

In the above, the method for controlling the watch type mobile terminal using a plurality of taps applied to the band unit 302 has been described. Meanwhile, the watch type mobile terminal may exchange information, through communication, with a mobile terminal (hereinafter, referred to as 'another terminal') of a bar type, a slide type, a folder type, or the like. Through the information exchange, the watch type mobile terminal and the other terminal may simultaneously perform the same function, or any one terminal may control another terminal. Further, through the information exchange, any one of the watch type mobile terminal and the other terminal may process and identify an event occurring in the other terminal.

As an example, in the watch type mobile terminal according to the present disclosure, another terminal communicating with the watch type mobile terminal may also controlled based on a plurality of taps applied to the band unit. Here, the watch type mobile terminal and the other terminal may perform communication in various schemes. The communication scheme between the watch type mobile terminal and the other terminal may be at least one of schemes including Bluetooth™, radio frequency identification (RFID), infrared data association (IrDA), ultra wideband (UWB), ZigBee, near field communication (NFC), wireless-fidelity (Wi-Fi), Wi-Fi direct and wireless universal serial bus (wireless USB).

Whether the other terminal is also to be controlled based on taps applied to the band unit may be determined based on the number of touch points included in a plurality of taps applied to the band unit. As described above, if the number of touch points included in one tap among a plurality of taps is different from that of touch points included in another tap, the taps may be recognized as different patterns.

As a representative example, a function of switching a locking state to a release state of the watch type mobile terminal through taps applied to the band unit will be described. The controller may determine whether to control only the watch type mobile terminal or whether to control together the watch type mobile terminal and the other terminal, based on the number of touch points included in taps corresponding to a pattern matched to the function of switch the locking state to the release state of the watch type mobile terminal.

As such, a terminal of which locking state is to be switched to the release state may be determined based on the number of touch points included in a plurality of taps.

Figure 5A:
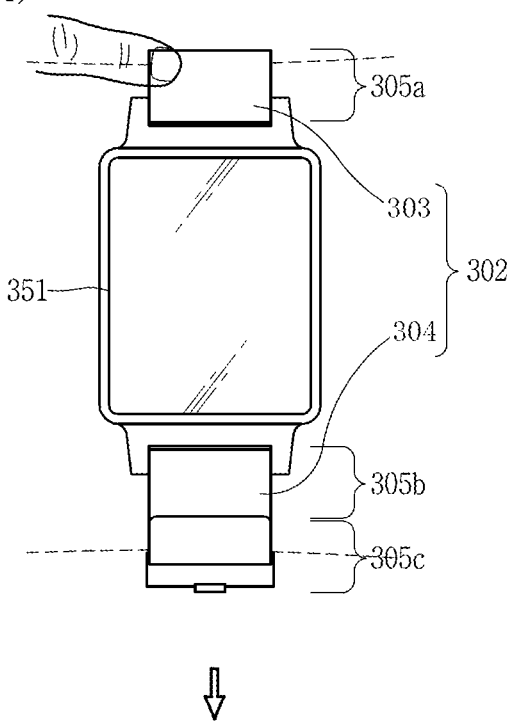
FIGS. 5A, 5B, 6A, 6B are conceptual diagrams illustrating a representative exemplary embodiment in which the mobile terminal is controlled using a user input applied to a band unit.
Figure 5A:
Figure 5A:
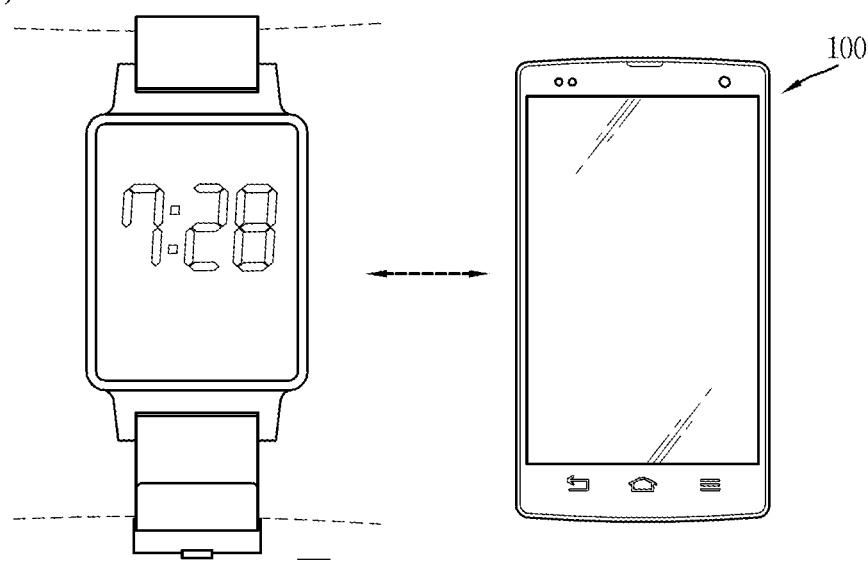

More specifically, if a release pattern matched to the function of switching the locking state to the release state is made through a plurality of taps including one touch point, the controller, as shown in FIG. 5A (a) and (b), may control only the locking state of the watch type mobile terminal. When the other terminal is in the locking state at the time when the taps are applied, the locking state of the other terminal may be continuously maintained even though the taps are applied.

Figure 5B:
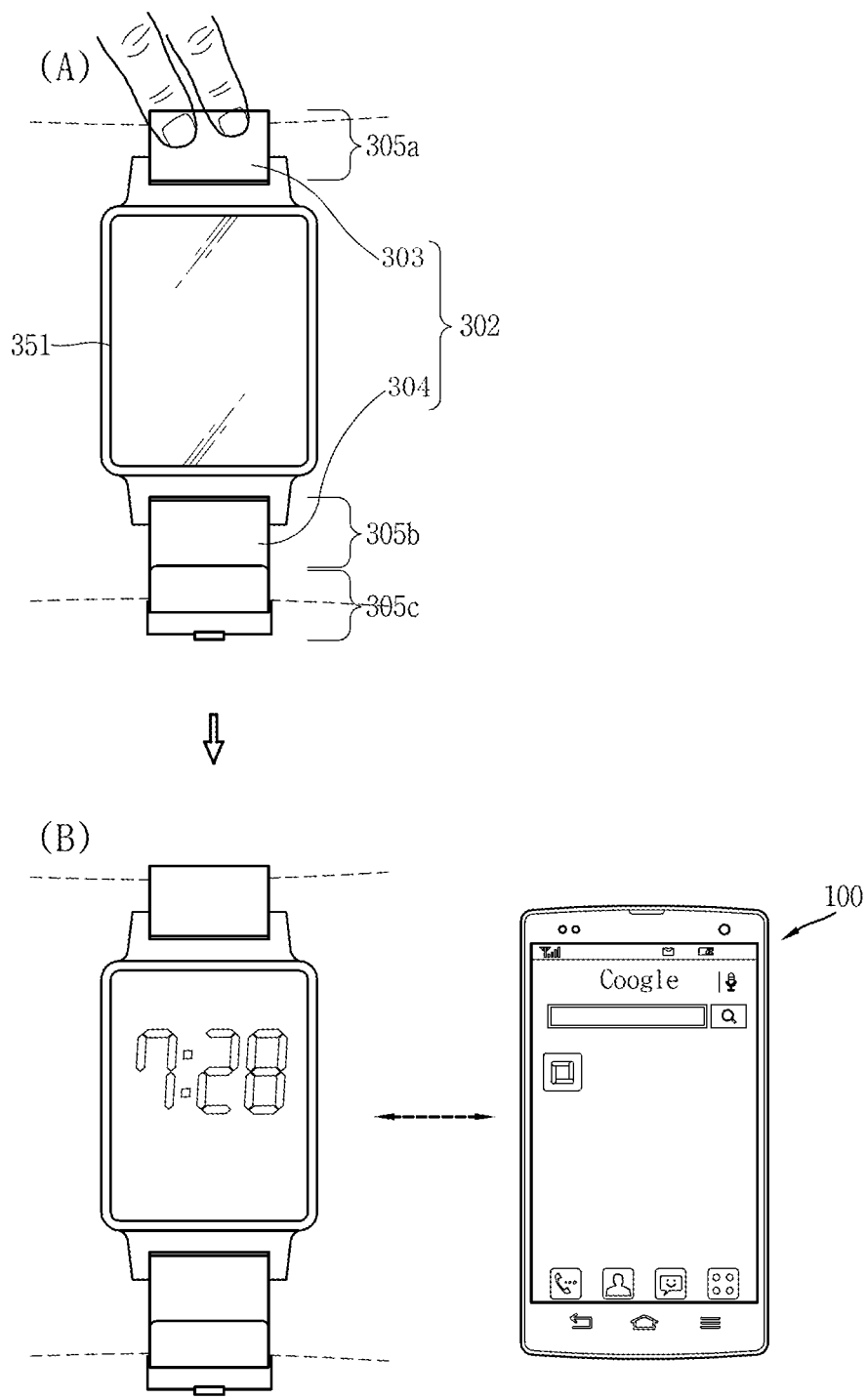

Further, as shown in FIG. 5B (a) and (b), if the release pattern is made through a plurality of taps including two touch points, the controller may simultaneously control the locking state of the watch type mobile terminal and the locking state of the other terminal paired with the watch type mobile terminal. When the other terminal is in the locking state at the time when the taps are applied, the locking state of the other terminal may be switched to the release state, corresponding to that the taps are applied. That is, if the release pattern is made through a plurality of taps including two touch points, the controller may transmit, to the other terminal, a control signal corresponding to a locking release command.

Meanwhile, although not shown in these figures, when the locking state of the other terminal is switched to the release state, based on taps applied to the watch type mobile terminal, notification information may be output to at least one of the watch type mobile terminal and the other terminal.

In this state, the controller of the watch type mobile terminal may output notification information including at least one of contents for notifying that the locking state of the other terminal has been released and contents for notifying that the locking state of the watch type mobile terminal and the locking state of the other terminal have been released together. Here, the notification information may be output in at least one of visual, tactile and auditory manners.

The notification information may be made in the form of a text, moving picture or image.

Further, the controller of the other terminal may output notification information including at least one of contents for notifying that the locking state of the other terminal has been released through control of the watch type mobile terminal and contents for notifying that the locking state of the watch type mobile terminal has also been released. Here, the notification information may be output in at least one of visual, tactile and auditory manners.

Meanwhile, although not shown in these figures, the watch type mobile terminal may determine the number of terminals to be controlled, based on the number of touch points included in a plurality of taps. For example, when a plurality of taps including two touch points are sensed, the controller may control one terminal. When a plurality of taps including three touch points are sensed, the controller may control two terminals.

Here, the kind of another terminal to be controlled by the watch type mobile terminal may be based on predetermined information. The user may previously select the kind of another terminal to be controlled by the watch type mobile terminal, and the controller may determine the other terminal to be controlled based on the user's selection.

Meanwhile, which another terminal is to be first controlled based on the number of user's fingers may be determined based on predetermined priority order information. In this case, the priority order information may be based on a user's selection.

As still another example, in the watch type mobile terminal according to the present disclosure, the communication scheme of the watch type mobile terminal with another terminal may be controlled based on the kind of pattern formed by a plurality of taps.

Figure 6A:
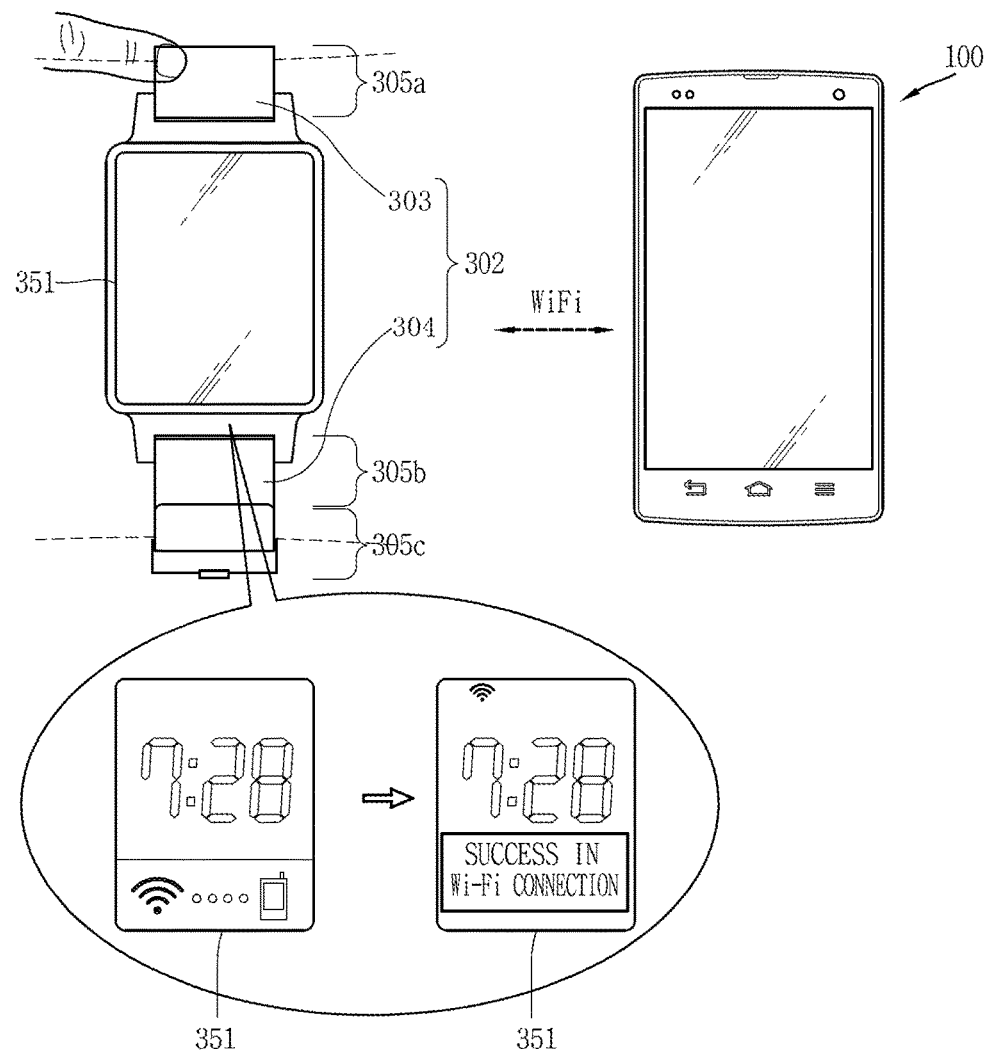
Figure 6B:
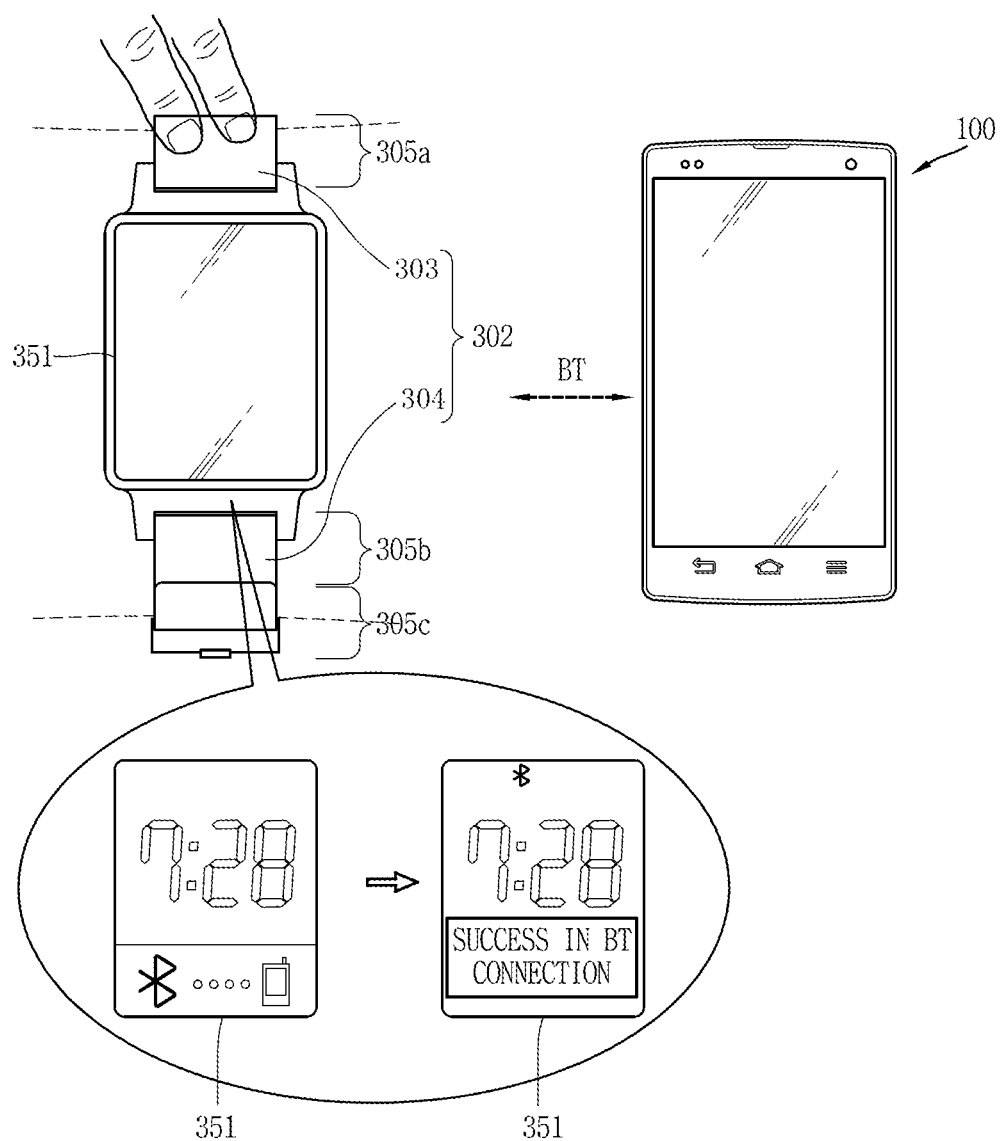

For example, as shown in FIG. 6A, when a plurality of taps corresponding to a first pattern are sensed, the controller may perform pairing with another terminal to communicate with the other terminal through a first communication scheme (e.g., a Wi-Fi scheme). As shown in FIG. 6B, when a plurality of taps corresponding to a second pattern different from the first pattern are sensed, the controller may perform pairing with the other terminal to communicate with the other terminal through a second communication scheme (e.g., a Bluetooth scheme) different from the first communication scheme.

Here, the patterns respectively corresponding to the first and second communication schemes may be patterns having different numbers of touch points included in taps while having the same order in which the taps are applied.

Meanwhile, as shown in FIGS. 6A and 6B, if the pairing between the terminals is completed, the controller may output notification information for notifying that the pairing has been completed through at least one of auditory, tactile and visual manners. Further, the controller may output a notification for notifying that it is in the process of performing pairing between the terminals through at least one of the auditory, tactile and visual manners.

Still another example of using a plurality of touch points will be described. In the watch type mobile terminal according to the present disclosure, although a pattern having the same order and number of times, where taps are applied to a plurality of areas assigned to at least one of the main body 301 and the band unit 302, is formed, different functions may be performed based on the number of touch points included in the taps.

For example, when a specific pattern is configured with taps including one touch point, the controller may perform a first function assigned to the specific pattern. When the specific pattern is configured with taps including two touch points, the controller may perform a second function different from the first function assigned to the specific pattern. Here, the first function may be execution of an exercise mode for performing a function related to exercise, and the second function may be execution of a health care mode for performing a function related to health care.

When the first function is performed, a pedometer function may be performed. Alternatively, when the second function is performed, a blood pressure check function may be performed.

Meanwhile, in the present disclosure, a plurality of patterns may exist, and different functions may exist to be linked with the respective patterns. In this case, a function to be linked with a pattern may be selected by the user.

Meanwhile, in the present disclosure, specific patterns configured with taps including different touch points may be referred to as different patterns, based on the number of touch points included in the taps forming the specific pattern.

In the above, the method for controlling the watch type mobile terminal using a plurality of taps applied to the band unit 302 has been described.

Figure 7A:
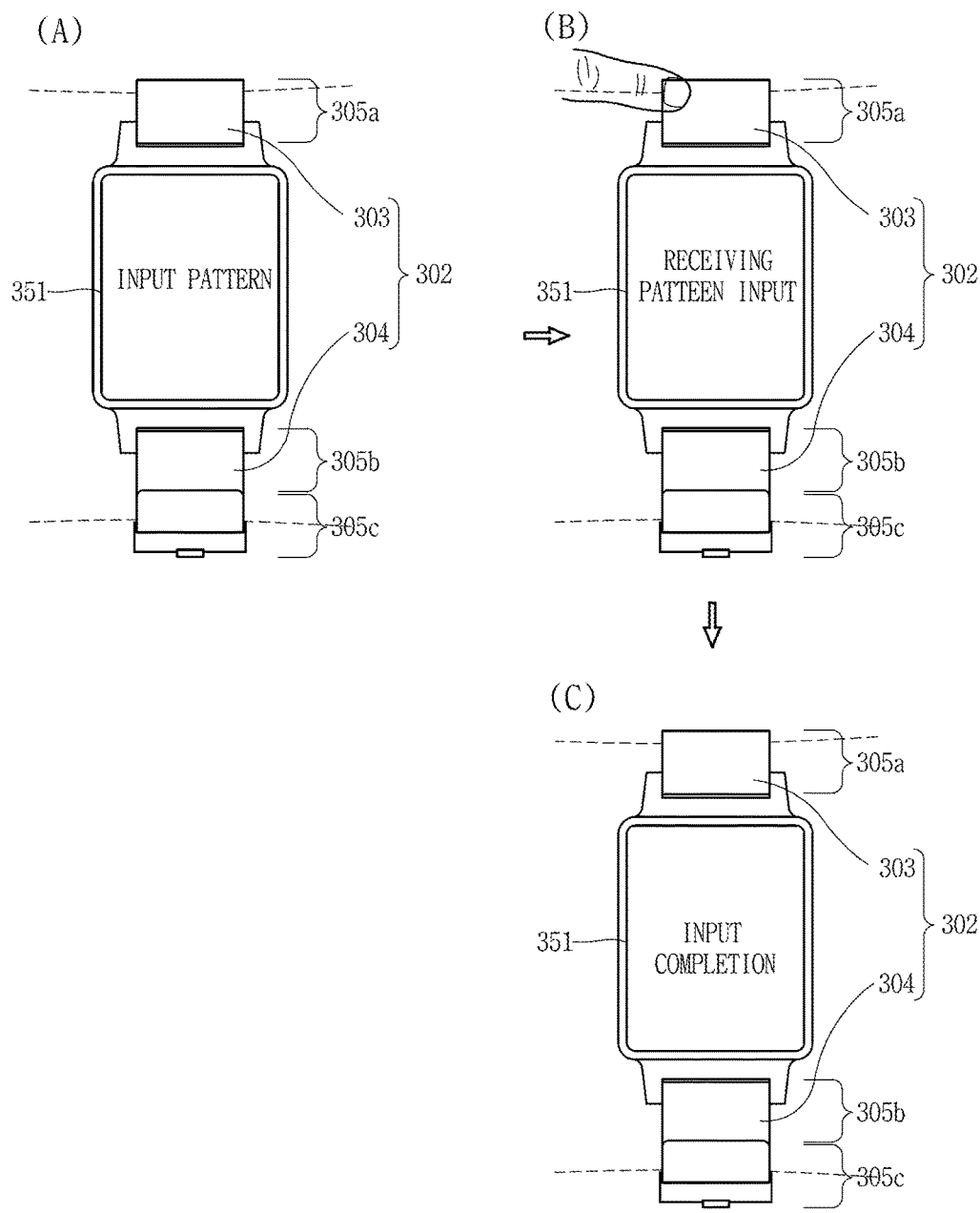
FIGS. 7A to 7C are conceptual diagrams illustrating a method for setting a pattern.
Figure 7B:
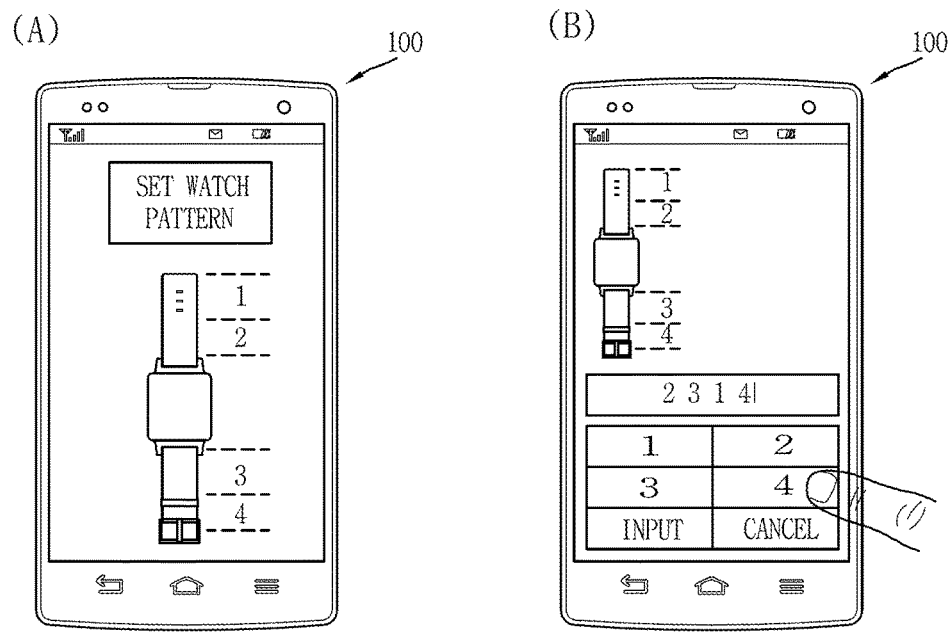
Figure 7C:
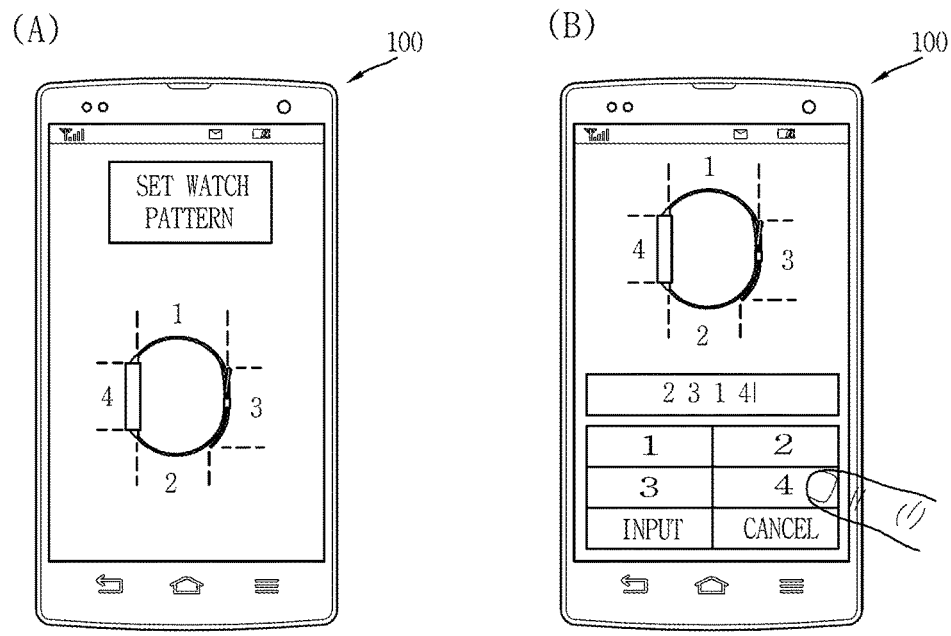

Hereinafter, a method for setting a pattern will be described in detail with reference to the accompanying drawings. FIGS. 7A to 7C are conceptual diagrams illustrating a method for setting a pattern.

As described above, a pattern may be defined by sequentially tapping at least one area of the band unit 302 divided into a plurality of areas. The pattern, as shown in FIG. 7A (a) and (b), may be set by a user's input. The controller may output a guidance screen or information for guiding pattern setting, based on a user's request. Here, the pattern may be configured to include taps with respect to the main body 301, as well as the band unit 302.

As shown in these figures, if a pattern setting completion command is received after a plurality of taps are applied to the band unit in a pattern setting mode, the controller may store, as a pattern, an area and order where the plurality of taps input in the pattern setting mode are applied. The controller may additionally receive, from the user, a function to be performed when the pattern is input.

Further, as described above, a plurality of areas included in the band unit 302 may be respectively matched to different numerals, and the controller may decide that a pattern is input through receiving a numeral from the user.

In this case, a graphic user interface (GUI) screen may be output on the display unit 351, in order to guide the user, information on a numeral assigned to each area of the band unit.

Meanwhile, as shown in FIGS. 7B and 7C, a pattern to be used in the watch type mobile terminal may be set in another terminal communicable with the watch type mobile terminal. As shown in these figures, numerals may be input on the other terminal. The numerals may be respectively linked with areas of the band unit 302.

In this case, information on which numeral is to be linked with each area of the band unit 302 may be output on the display unit of the watch type mobile terminal or the other terminal.

For example, when the user intends to set a password for releasing a locking state, the user may set the password with 'numerals' on the other terminal. The numerals may be respectively matched to a plurality of areas of the band unit 302. Therefore, when areas corresponding to the numerals that correspond to the set password are sequentially tapped in the band unit 302, the locking state may be released.

In this case, the password may be commonly applied to the other terminal and the watch type mobile terminal. For example, when the set password is input to the other terminal, the locking state of the other terminal may be released. When a plurality of taps corresponding to a pattern that corresponds to the set password are applied to the watch type mobile terminal, the locking state of the watch type mobile terminal may be released.

Meanwhile, although not shown in these figures, a pattern previously set in another terminal may be used even though a pattern of the watch type mobile terminal is not separately set on the other terminal.

Here, the pattern previously set in the other terminal may be a pattern for controlling a function of the other terminal. For example, in the other terminal, the locking state may be switched to the release state, based on a predetermined pattern formed by at least one tap applied to the main body including the display unit of the other terminal in a state in which the display unit of the other terminal is off.

The main body of the other terminal may be divided into a plurality of areas, and a pattern formed by taps sequentially applied to at least one of the plurality area may be formed by at least one of the positions, order and number of times of the taps.

In this case, the plurality of areas into which the main body of the other terminal is divided may respectively correspond to those of the watch type mobile terminal. When the pattern previously set in the other terminal is applied to the plurality of areas of the watch type mobile terminal, respectively corresponding to the plurality of areas into which the main body of the other terminal is divided, a function of the watch type mobile terminal may be controlled. Here, the function may be a function of switching the locking state to the release state.

Meanwhile, which area of the watch type mobile terminal each of the plurality of areas into which the main body of the other terminal is divided is to correspond to may be determined based on a user's selection. Further, in at least one of the other terminal and the watch type mobile terminal, guidance information capable of identifying which area of the watch type mobile terminal each of the plurality of areas into which the main body of the other terminal is divided corresponds to may be provided based on a user's request.

Meanwhile, the controller of the watch type mobile terminal may control the watch type mobile terminal, using taps corresponding to a pattern set in the other terminal only in a state in which the watch type mobile terminal is paired with the other terminal.

Figure 8A:
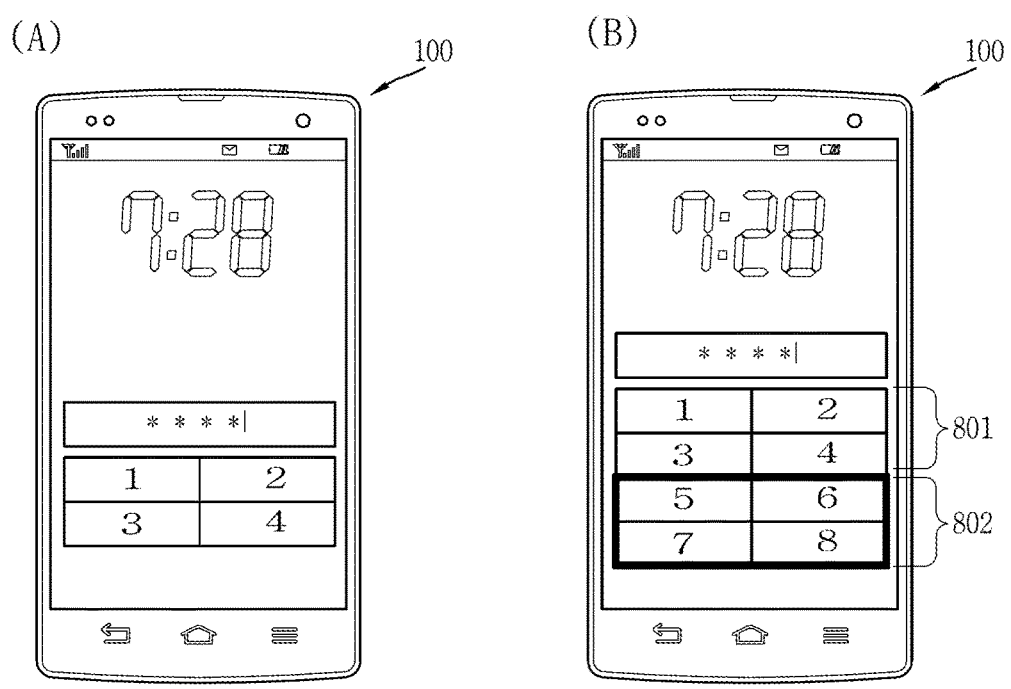
FIGS. 8A and 8B are conceptual diagrams illustrating a method for controlling the watch type mobile terminal in another terminal.
Figure 8B:
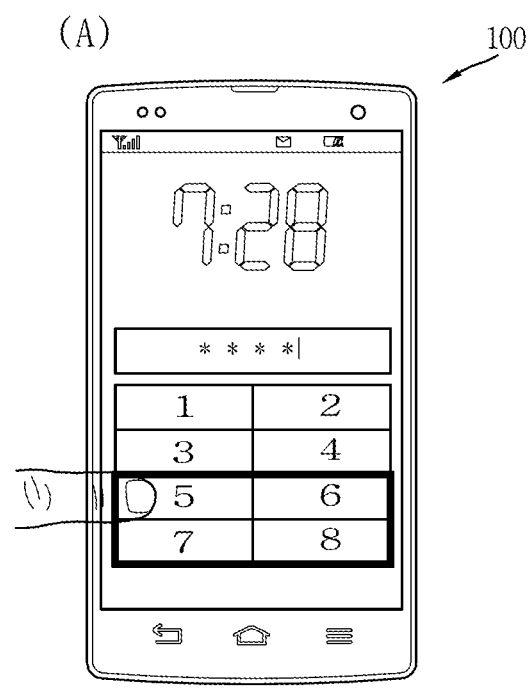
Figure 8B:
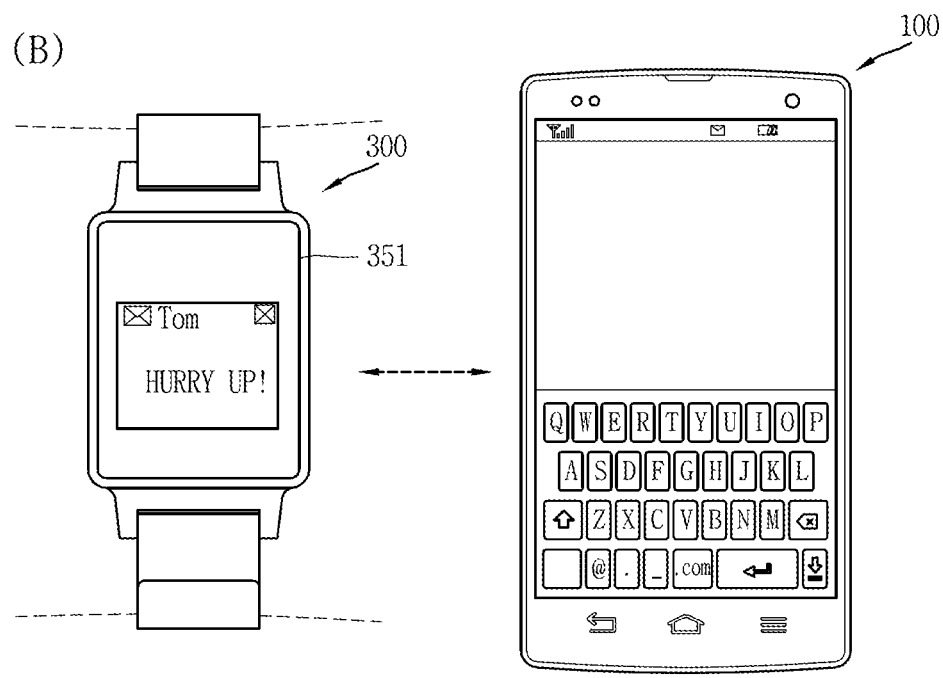

Hereinafter, a method for controlling the watch type mobile terminal through another terminal will be described in detail with reference to the accompanying drawings. FIGS. 8A and 8B are conceptual diagrams illustrating a method for controlling the watch type mobile terminal in another terminal.

The watch type mobile terminal according to the present disclosure may be controlled through another terminal paired with the watch type mobile terminal. As a representative example, the locking state of the watch type mobile terminal may be switched to the release state through a user input in the other terminal. When the other terminal is paired with the watch type mobile terminal, a control screen for controlling the locking state of the watch type mobile terminal may be additionally output. For example, as shown in FIG. 8A (a), a locking screen for controlling the locking state of the other terminal is output on the locking screen of the other terminal before the watch type mobile terminal is paired with the other terminal. As shown in FIG. 8A (b), the locking screen for controlling the locking state of the other terminal and a locking screen for controlling the locking state of the watch type mobile terminal may be output together on the locking screen of the other terminal after the watch type mobile terminal is paired with the other terminal.

As shown in FIG. 8A (b), the locking screen may include a plurality of areas, and the locking state of at least one of the other terminal and the watch type mobile terminal may be controlled through a user input with respect to each of the plurality of areas.

For example, the locking state of the other terminal may be controlled through a user input with respect to a first area 801, and the locking state of the watch type mobile terminal may be controlled through a user input with respect to a second area 802.

If a password is input through any one of the first and second areas 801 and 802, the controller of the other terminal waits for a user input with respect to another area for a predetermined time. If any user input is not applied for the predetermined time, the controller controls the locking state of a terminal corresponding to the area to which the user input is applied. If a user input for controlling the locking state of the watch type mobile terminal is applied in the other terminal, the controller of the other terminal may transmit, to the watch type mobile terminal, a control signal related to the locking state of the watch type mobile terminal.

Further, when only a user input for releasing the locking state of the watch type mobile terminal is applied on the other terminal as shown in FIG. 8B (a), the other terminal may be used as an input means of the watch type mobile terminal as shown in FIG. 8B (b). In this case, information input through the other terminal may be transmitted to the watch type mobile terminal. Therefore, the other terminal may be used as a keyboard of the watch type mobile terminal.

Meanwhile, the area in which the user input for releasing the locking state of the watch type mobile terminal is applied on the other terminal may be displayed to be distinguished from that in which a user input for releasing the locking state of the other terminal is applied, so that the user can distinguish the areas from each other.

Figure 9A:
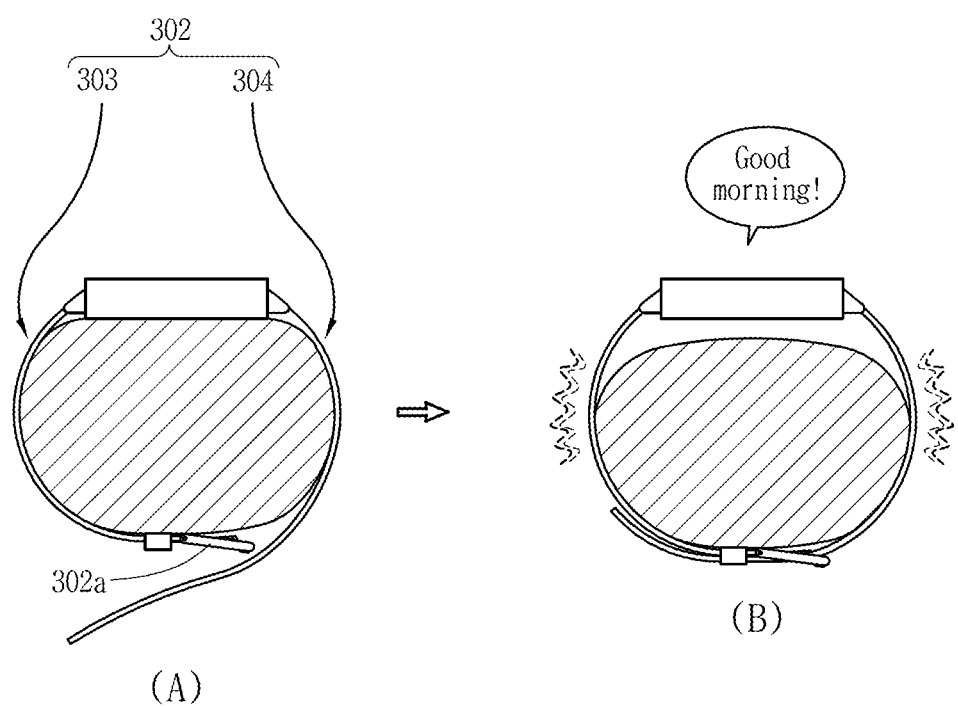
FIGS. 9A and 9B are conceptual diagrams illustrating a method for sensing a user input with respect to the band unit.
Figure 9B:
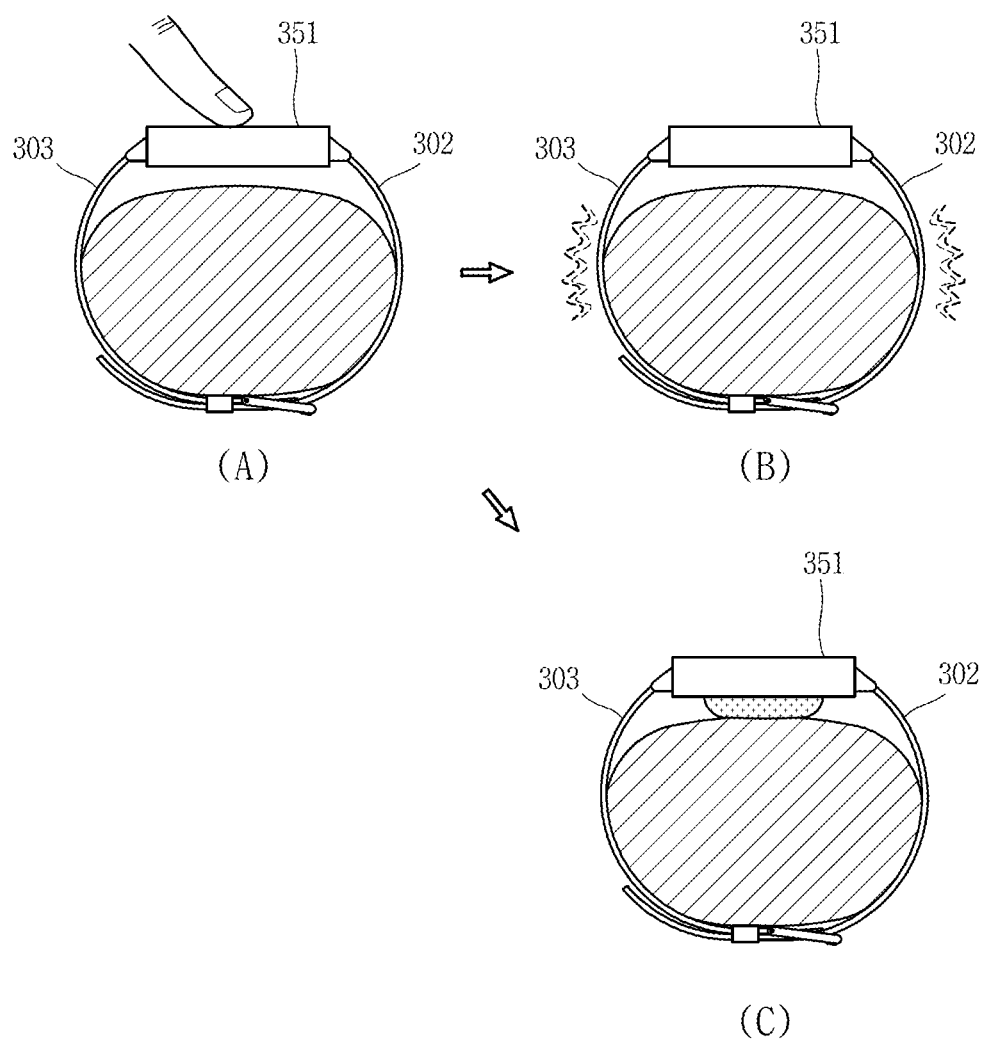

Hereinafter, a method for sensing a user input with respect to the band unit will be described in detail with reference to the accompanying drawings. FIGS. 9A and 9B are conceptual diagrams illustrating a method for sensing a user input with respect to the band unit.

As described above, the watch type mobile terminal according to the present disclosure may process taps with respect to the band unit as a user input with respect to the watch type mobile terminal.

That is, at least one sensor capable of sensing taps may be included in the band unit. The sensor may be activated only when the fastening state of the band unit satisfies a specific condition, or the controller may process taps with respect to the band unit as a user input only when the fastening state of the band unit satisfies the specific condition.

First, referring to FIG. 9A, if the first and second bands 303 and 304 are connected to each other by the fastener 302a in a state in which the band unit 302 is wound around a wrist, thereby forming a third area 305c, the sensing unit may be activated. In other words, if the band unit 302 is contacted with skin as the watch type mobile terminal is worn on the wrist, the sensing unit may be activated. A function of sensing a user input is activated in the band unit by the activation of the sensing unit.

Here, the specific condition may mean that the first and second bands 303 and 304 are connected to each other by the fastener 302a, thereby forming the third area 305c.

As an example, as shown in FIG. 9A (b), the controller may generate a feedback for notifying the activation of the sensing unit. The feedback, as shown in this figure, may become generation of vibration. As another example, the controller may generate, as sound notification, a predetermined notification sound such as 'Good morning!'. As still another example, the controller may notify that the band unit starts sensing a user input using screen conversion, or the like.

Meanwhile, although not shown in these figures, the controller may perform different controls, based on whether the user wearing the watch type mobile terminal is a proper user, even when the first and second bands 303 and 304 are fastened to each other by the fastener 302a.

User information of the watch type mobile terminal may be stored in the memory 170. If the first and second bands 303 and 304 are fastened to each other by the fastener 302a, the controller may perform a process of authenticating a user wearing the watch type mobile terminal, based on the user information. Here, the authentication process may be performed through at least one of face recognition, fingerprint recognition, iris recognition and wrist thickness recognition.

As an example, when it is authenticated, through the wrist thickness recognition, that the user wearing the watch type mobile terminal is not a proper user, the controller may control the band unit of the watch type mobile terminal, to loosen the band or release the fastening between the first and second bands 303 and 304 by the fastener 302*a* so that the watch type mobile terminal is not worn on a wrist of the improper user.

Here, the band unit contains an electric active polymer material, and loosening or tightening of the band unit may be implemented by controlling the supply of power to the electric active polymer material.

As another example, when it is authenticated that the user wearing the watch type mobile terminal is not a proper user, the controller may limit access to at least one function by executing the guest mode described above. Meanwhile, the execution of the guest mode may be made only when taps corresponding to a predetermined pattern for controlling a locking state or specific function are sensed in the state in which the improper user wears the watch type mobile terminal. In other cases, the fastening between the first and second bands 303 and 304 by the fastener 302*a* may be released, or the band unit may be loosened.

Meanwhile, the wrist thickness recognition may be made through information on the position at which the first and second bands 303 and 304 are fastened to each other by the fastener 302*a* and information sensed by at least one of touch sensors disposed inside the band unit. Here, the touch sensor may be configured with an ITO touch film.

As such, according to the present disclosure, when it is authenticated that the user wearing the watch type mobile terminal is not a proper user, the use of the watch type mobile terminal is limited, thereby further enhancing user's privacy protection.

As still another example, the controller may provide each user with an optimized use environment through a process of authenticating a user wearing the watch type mobile terminal.

For example, the watch type mobile terminal may be used by several users, and user information on a plurality of users may be stored in the memory 170.

Here, the user information may include information related to the use of the watch type mobile terminal of a corresponding user, including authentication information for authenticating the corresponding user through the watch type mobile terminal, information on a function frequently used by the corresponding user, information on a function frequently set by the corresponding user, information on another terminal paired with the watch type mobile terminal by the corresponding user, and the like.

As described above, the process of authenticating the user may be performed through at least one of face recognition, fingerprint recognition, iris recognition and wrist thickness recognition.

As an example, when a specific user is authenticated through the wrist thickness recognition, the controller may perform pairing with at least one another terminal used by the specific user with reference to the user information. As described above, the wrist thickness recognition may be made through information on the position at which the first and second bands 303 and 304 are fastened to each other by the fastener 302*a* and information sensed by at least one of touch sensors disposed inside the band unit. Here, the touch sensor may be configured with an ITO touch film.

The specific condition may correspond to that the display unit 351 of the watch type mobile terminal is tapped or touched as many as a predetermined number of times. For example, if the display unit 351 is tapped as many as the predetermined number of times as shown in FIG. 9B (a), the controller may generate a feedback for notifying activation of the sensing unit as shown in FIG. 9B (b). The feedback, as shown in this figure, may become generation of vibration.

Further, the controller, as shown in FIG. 9B (c), may control the band unit to tighten the wrist, thereby generating a feedback for notifying activation of the sensing unit. The tightening feeling may be provided as an electric active polymer material is contained in the band unit, and the supply of power to the electric active polymer material is controlled. Meanwhile, the tightening of the band unit may be applied to the case described in FIG. 9A.

Meanwhile, in the exemplary embodiments described above, the method for switching the locking state to the release state through taps of the band unit has been described as a representative example. The present disclosure may provide various functions in addition to the function of releasing the locking state through taps with respect to the band unit, and the user input with the band unit may be made in various manners, in addition to the taps described above.

Hereinafter, more various user input methods and functions will be described in detail with reference to the accompanying drawings. FIGS. 10A to 10D are conceptual diagrams illustrating kinds of user inputs using the band unit.

The controller may process different control commands based on an area to which a user input is applied among a plurality of areas divided in the band unit 302. That is, the controller may process different control commands, based on which area among the first, second and third areas 305*a*, 305*b* and 305*c* an input (e.g., a short touch) of the same form is sensed in.

The controller may process different control commands, based on which type of input (e.g., a short touch, long touch, drag, bend or flip) is sensed even in the same area. As an example, the user input may be a touch input applied to the band unit, and the controller may process different control command based on a kind of the touch input applied to the same area of the band unit.

As another example, if first and second tappings (or first and second touches) are consecutively applied to the band unit, the controller may control the terminal to be in a ready state (or an activation state), corresponding to that the first tapping is sensed. When the second tapping is again applied, the controller may generate a control signal to control the terminal, corresponding to that the second tapping is sensed, and process a corresponding control command. That is, the user first applies the first tapping, to transmit, to the terminal, information that the terminal is controlled using the tapping.

The control command may be, for example, a command for activating the display unit 351 or a command performed in the state in which the display unit 351 is activated. In this case, a GUI output on the display unit 351 by the user input may be controlled. As a more specific example, graphic images to be selected may be included in the GUI, and any one of the graphic images may be selected by the user input. As another example, a function linked with an execution screen of an application being executed by the user input may be performed, and screen information related to the linked function may be output on the display unit 351.

In the present disclosure, the control command may be processed in response to the user input even in the state in which the display unit 351 is non-activated. In this case, a wake-up signal may exist so that a touch with respect to the band unit is received as the user input. As an example, the wake-up signal may be generated by a user input applied to another portion in a state in which the sensor disposed in the band unit is non-activated, or may be generated by the initial tapping (the first tapping of the first and second tappings) among the tappings consecutively applied to the band unit. As another example, the wake-up signal may be generated by a control command applied through a voice or a control command applied through movement of the terminal. In this case, operation control for the terminal may be performed corresponding to a user input sensed after the wake-up signal is applied.

Further, different control commands may be respectively linked with various types of user inputs with respect to the band unit. Thus, the user can control various functions through the user inputs with respect to the band unit.

As an example, the function executed by the user input applied to the band unit may be a function linked with an application being currently executed or a function related to a current operation of the terminal. As another example, the user input may become a specific function specified to at least one of a sensed area and a kind of the input. In this case, different functions may be performed based on the area and kind. For example, a touch input applied to the band unit 302 may become a short touch, long touch, tapping, drag, swipe or the like, and a physical input may become an input accompanied with bend (or movement) of the band unit.

Hereinafter, several user inputs applied to the band unit to perform the aforementioned functions will be described. That is, at least one of the aforementioned functions may be performed in response to several user inputs described below. Only some of the several user inputs may be applied in the terminal, and the others may not be applied in the terminal. In addition, different controls may be performed with respect to some user inputs to be applied.

Figure 10A:
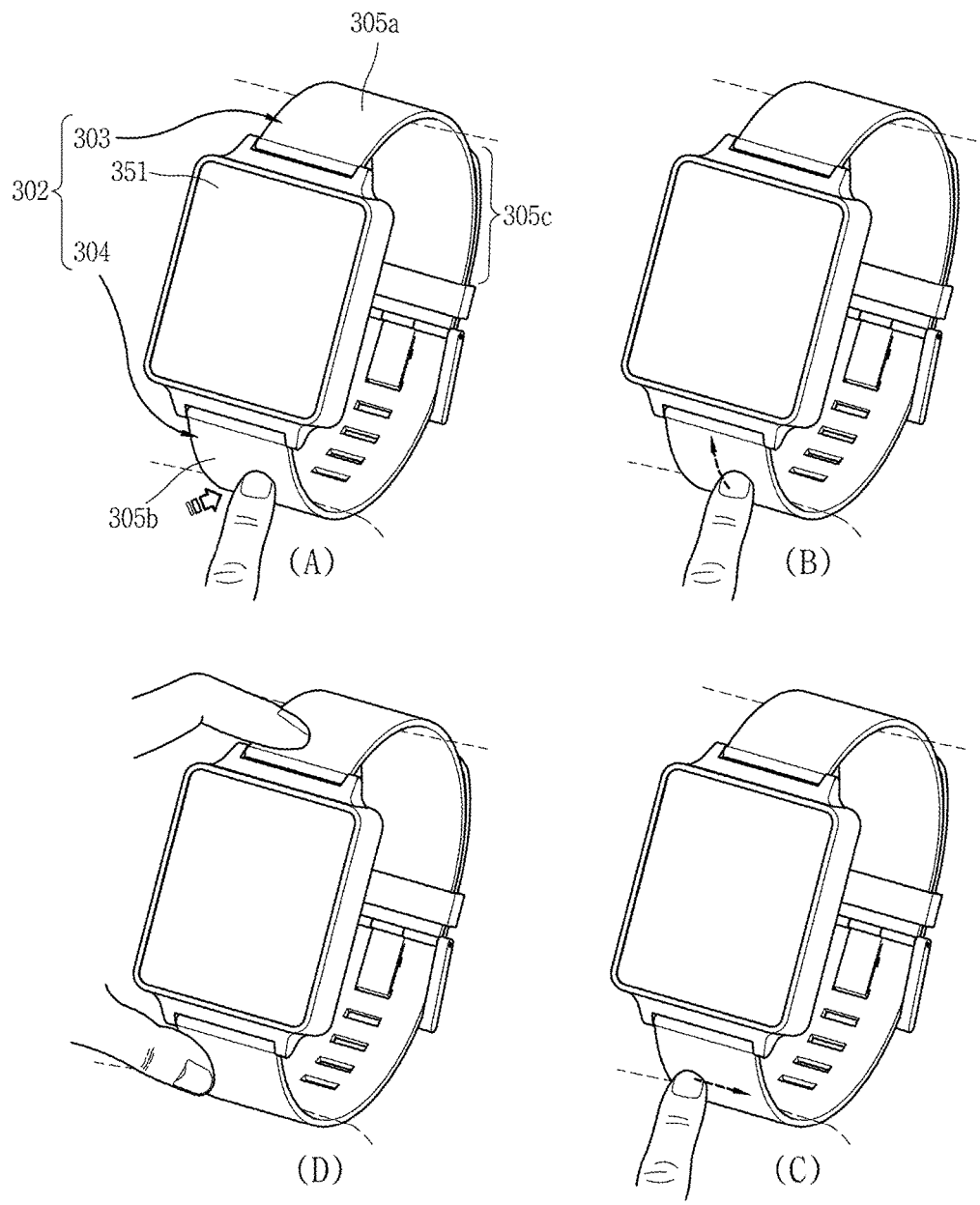
FIGS. 10A to 10D are conceptual diagrams illustrating kinds of user inputs using the band unit.

As an example, referring to FIG. 10A (a), a touch input sensed in the band unit 302 may become a short touch, a tapping or a long touch applied for a predetermined time or more. The short touch, tapping, long touch and the like may be sensed in at least one of the first and second bands 303 and 304.

As another example, referring to FIG. 10A (b), a touch input sensed in the band unit may become a drag applied along one direction. The touch input may be sensed as a drag applied along the length direction of the band unit in at least one of the first and second bands 303 and 304. More specifically, at least one of the aforementioned functions may be performed by a drag applied from the top to the bottom or from the bottom to the top in at least one of the first and second bands 303 and 304.

As still another example, referring to FIG. 10A (c), the drag may be sensed as a drag applied along the width direction (direction perpendicular to the length direction) of the band unit in at least one of the first and second bands 303 and 304. More specifically, at least one of the aforementioned functions may be performed by a drag applied from the left to the right or from the right to the left.

As still another example, referring to FIG. 10A (d), at least one of the aforementioned functions may be performed by a touch input simultaneously applied to two areas among a plurality of areas of the band unit 302. Specifically, the touch input sensed in the band unit 302 may become a short touch, a tapping or a long touch applied for a predetermined time or more, which is simultaneously applied to the first and second areas 305a and 305b (or simultaneously applied to the first and second bands 303 and 304). The touch input sensed in the band unit 302 may become a drag simultaneously applied to the first and second bands 303 and 304.

Figure 10B:
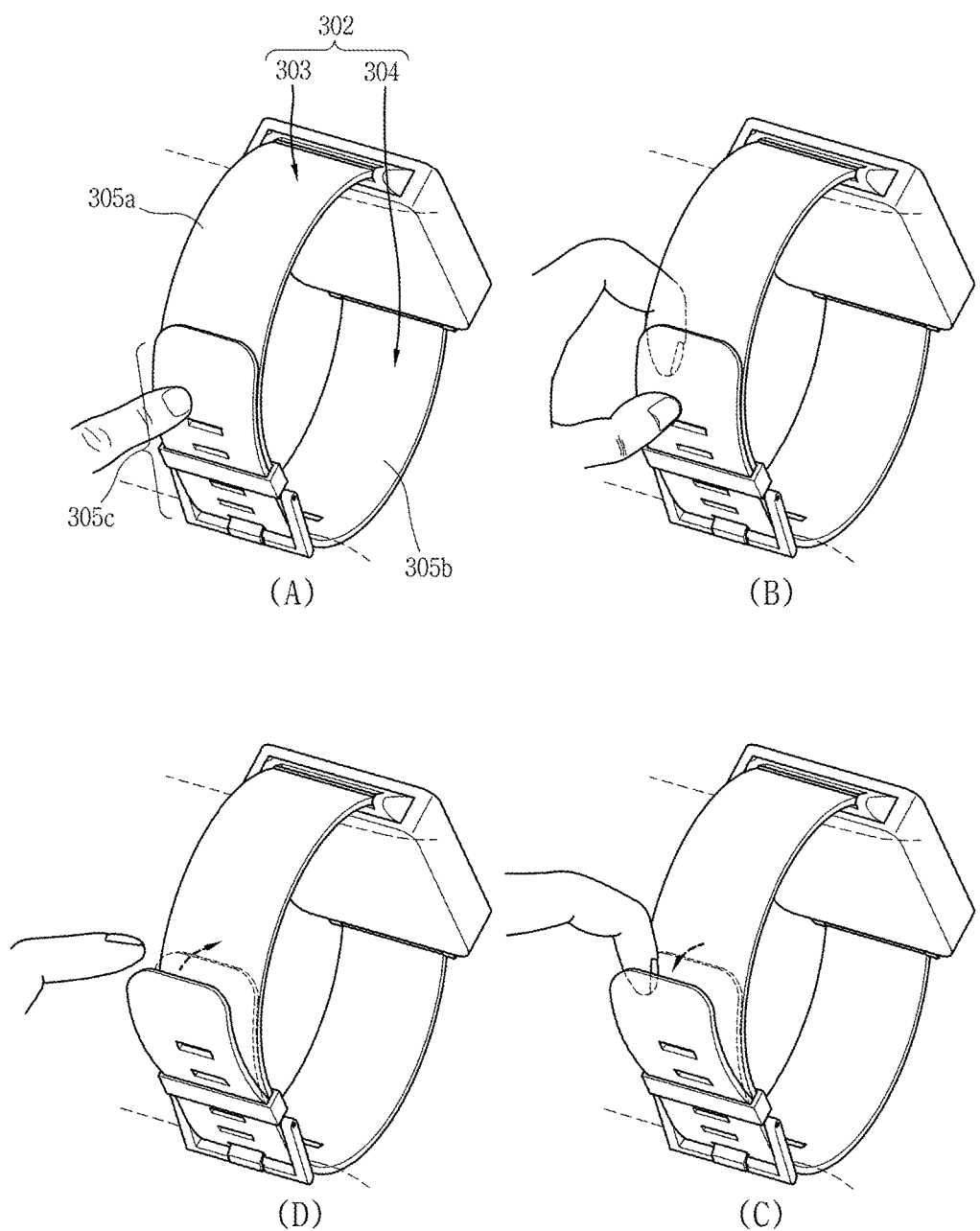

FIG. 10B is a conceptual diagram illustrating a method for processing several control commands using a double band portion formed by overlapping between the first and second bands 303 and 304, i.e., a third area.

Referring to FIG. 10B, a user input applied to the third area 305c by the user may become, for example, a touch input or physical input, and at least one of the aforementioned functions may be performed in response to the user input.

As an example, referring to FIG. 10B (a), the touch input sensed in the third area 305c may become a short touch, a tapping or a long touch applied for a predetermined time or more. In addition, a drag, swipe or the like applied to the third area 305c may become the touch input. More specifically, the short touch, tapping, long touch, drag, swipe and the like may be sensed at a portion corresponding to the third area 305c in the first and second bands 303 and 304. As shown in this figure, if any one of the short touch, tapping, long touch, drag and swipe is applied to the outer surface (surface opposite to the surface facing the wrist when the watch type mobile terminal is worn on the wrist) of the second band 304 when the second band 304 covers the first band 303 in the third area 305c, the controller may process this as a user input.

As another example, referring to FIG. 10B (b), at least one of the aforementioned functions may be performed by a touch input sensed from both surfaces of the band unit in the third area 305c. More specifically, if any one of the short touch, tapping, long touch, drag and swipe is applied to each of the outer surface of the second band 304 and the inner surface (surface facing the wrist when the watch type mobile terminal is worn on the wrist) of the first band 303 when the second band 304 covers the first band 303 in the third area 305c, the controller may process this as a user input.

As still another example, at least one of the aforementioned functions may be performed by a physical input sensed from the band unit in the third area 305c.

Referring to FIG. 10B (c), if any one of the first and second bands 303 and 304 is lifted in the third area 305c, the controller may process this as a user input. In this figure, it is illustrated that one end of the second band 304 is lifted by the lifting operation. The sensing unit may sense that the second band relatively moves with respect to the first band, or may sense that a bend occurs in the second band. Accordingly, the sensing unit can recognize that the second band 304 is lifted.

Referring to FIG. 10B (d), if any one of the first and second bands 303 and 304 is flipped in the third area 305c, the controller may process this as a user input (specifically, a flip input). In this figure, it is illustrated that one end of the second band 304 is flipped. To this end, if the force for lifting the one end of the second band is removed, the second band may be restored to the original position by the self-elasticity thereof.

However, the present disclosure may be applied even when the first band 303 covers the second band 304 in the third area 305c. In this state, the outer surface of the first band 303 may become an object of the touch input in FIG. 10B (a), and the inner surface of the second band 304 and the outer surface of the first band 303 may become objects of the touch input in FIG. 10B (b). In FIG. 10B (c) and (d), the first band 303 may become an object of the physical input.

Figure 10C:
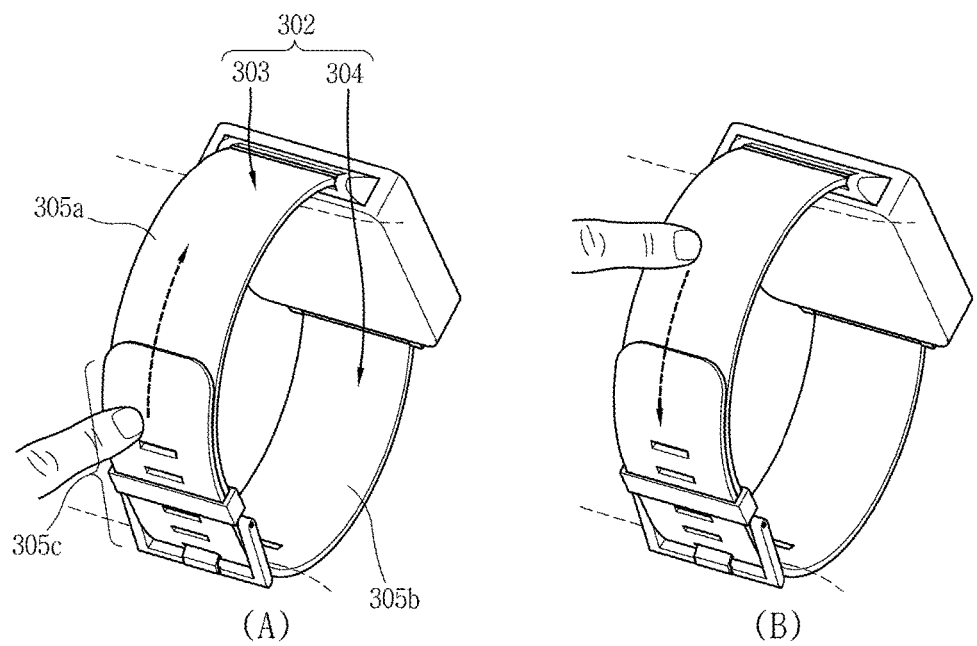
Figure 10C:
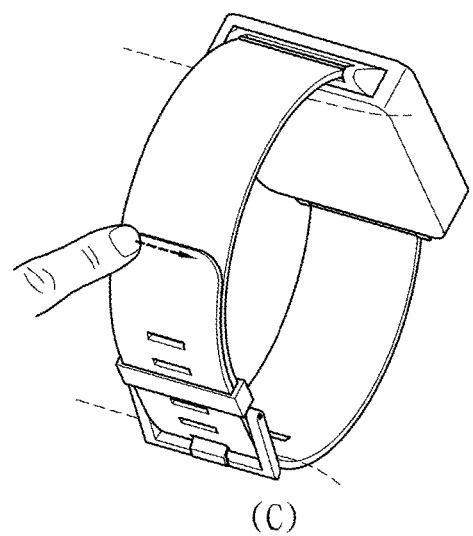

FIG. 10C is a conceptual diagram illustrating a method for processing several control commands using boundary portions between a plurality of areas.

Referring to FIG. 10C, at least one of the aforementioned functions may be performed in response to a touch input applied to a boundary portion of the third area 305c.

As an example, referring to FIG. 10C (a) and (b), after the band unit is touched, the controller may process, as a user input, a drag or swipe passing through the boundary portion of the third area 305c. In this case, the sensing unit may sense a direction of the drag or swipe, and different controls (first and second controls) may be performed based on the direction. As shown in FIG. 10C (a), the first control may be performed by a drag or swipe that starts from the third area 305c of the second band 304, passes through the boundary portion and then reaches the first area 305a of the first band 303. On the contrary, as shown in FIG. 10C (b), the second control may be performed by a drag or swipe that starts from the first area 305a of the first band 303, passes through the boundary portion and then reaches the third area 305c.

As another example, referring to FIG. 10C (c), the controller may process, as a user input, a drag or swipe that is applied to the boundary portion and progresses along the boundary line. That is, if a drag or swipe is applied along the width direction of the band unit, at least one of the aforementioned functions may be performed.

Figure 10D:
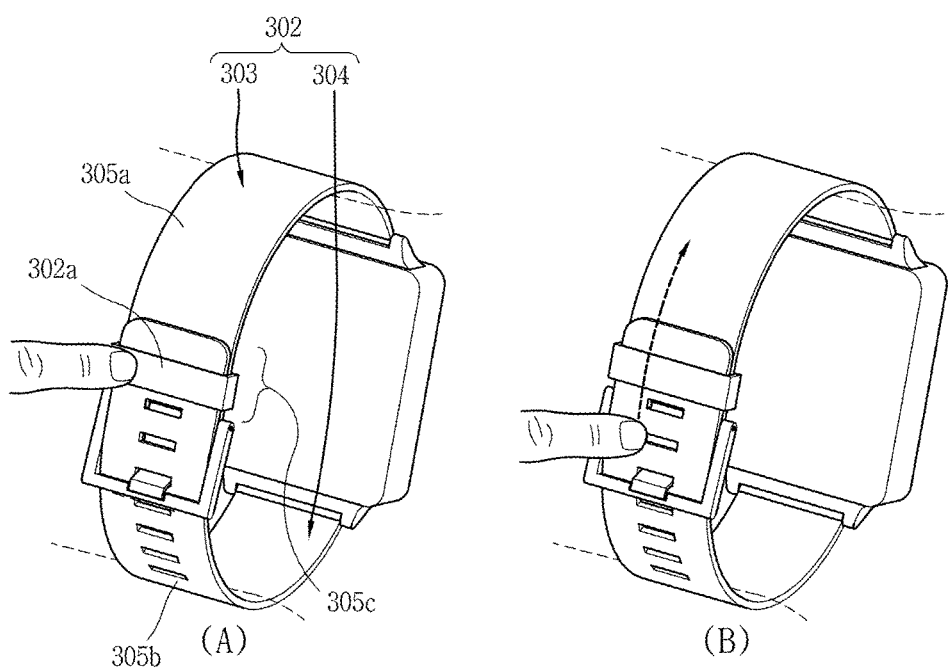

Next, a method for processing several control command using a portion adjacent to the third area will be described in detail with reference to FIG. 10D. FIG. 10D is a conceptual diagram illustrating a method for processing several control commands using a portion adjacent to the third area.

Referring to this figure, the length of the band unit 302 may be adjusted when the watch type mobile terminal is worn on the wrist, and the sizes of the first, second and third areas 305a, 305b and 305c may be changed by the length adjustment. In this case, if the size of the third area 305c is smaller than a predetermined value, the third area 305c may include another portion in addition to the portion at which the first and second bands 303 and 304 are overlapped with each other. Accordingly, the user can easily input a control command when the size of the third area 305c is small. In this case, the predetermined value is a reference value, and therefore, the portion at which a user input is sensed may be changed depending on the size of the third area 305c. However, the present disclosure is not necessarily limited thereto, and the example illustrated with reference to FIG. 10D may be applied to the present disclosure regardless of the size of the third area 305c.

As an example, referring to FIG. 10D (a), a user input with respect to the fastener 302a provided to the band unit 302 may also be processed like the input applied to the third area 305c. That is, the sensing unit may sense a touch, push, bend, flip or the like with respect to the fastener 302a, and the controller may perform at least one of the aforementioned functions in response to the sensing.

As another example, a user input applied to one band covered by another band may also be processed like the input applied to the third area 305c. The sensing unit may sense a touch, push, bend, flip or the like with respect to a portion adjacent to the fastener 302a in the first band 303, and the controller may perform at least one of the aforementioned functions in response to the sensing.

Referring to FIG. 10D (b), a continuous touch input in the first and second bands 303 and 304 may also be processed like the input applied to the third area 305c. More specifically, if one band covering another band (the second band in this example) or the fastener is touched and the band covered by the other band (the first band in this example) is then touched, the controller may perform at least one of the aforementioned functions in response to the continuous touch.

In this example, when the third area is an area connecting the first and second bands to be engaged with each other, the continuous touch input may become a touch applied to the same plane formed by the first band, the third area and the second band. The continuous touch input may become a touch applied to a boundary portion at which the first and second bands are engaged with each other. In this case, the touch may become a drag or swipe.

As described above, in the present disclosure, the terminal can be controlled using various input methods through the band unit, in addition to a method for controlling the terminal using a plurality of taps with respect to the band unit divided into a plurality of areas.

Figure 11:
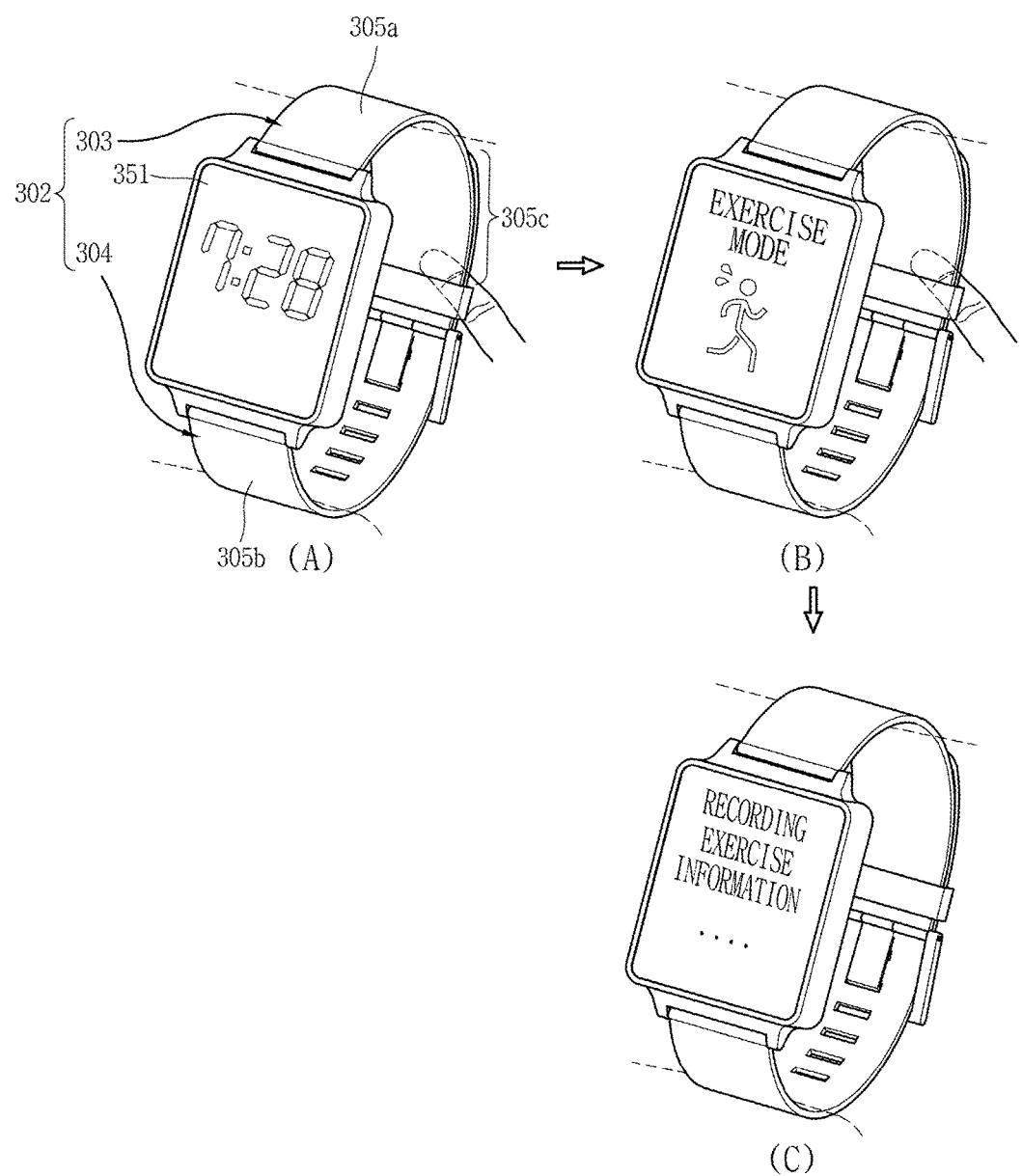
FIG. 11 is a conceptual diagram illustrating a method for controlling the band unit based on a function.

Meanwhile, in the present disclosure, the operation of the band unit may be controlled based on a currently performed function. FIG. 11 is a conceptual diagram illustrating a method for controlling the band unit based on a function.

In the present disclosure, a specific mode may be executed corresponding to a predetermined user input with respect to the band unit. Here, the specific mode may be matched to a specific user input. That is, if a specific user input is applied, the controller may execute the specific mode. The specific user input may be one of the methods described in FIGS. 10A to 10D or one of the patterns described in FIGS. 4A to 4E.

Here, the specific mode may be a mode for performing a function related to health, such as an exercise mode or a blood pressure check function. In the specific mode, when the band unit tightens the wrist, the function may be further maximized. Therefore, the controller may control the operation of the band unit in the specific mode. That is, as shown in FIG. 11 (a) and (b), when the specific mode is executed, the controller may control the band unit to tighten the wrist. The tightening feeling may be provided as an electric active polymer material is contained in the band unit, and the supply of power to the electric active polymer material is controlled.

Meanwhile, if an exercise mode is executed, an operation of recording exercise information, and the like may be performed. However, before the exercise mode is executed, another mode may be executed, or a sleep mode in which the display unit 351 is non-activated may be executed. If another user input is applied to the band unit while the exercise mode is being executed, another mode may be executed. More specifically, if a long touch is applied to the third area 305c, the exercise mode may be executed. If a touch covering at least one portion of the third and first areas 305c and 305a is applied, a blood pressure check mode for measuring a user's blood pressure may be executed.

The blood pressure check mode may be executed based on a user input applied to the band unit in a watch or sleep mode, rather than the exercise mode.

As such, the user input applied to the band unit may be any one of a plurality of touch inputs applied to the band unit, and each of the plurality of touch inputs may be defined as an execution command with respect to any one of a plurality of operation modes.

Further, the blood pressure check mode or exercise mode is executed by the touch in the state in which the display unit 351 is non-activated. In this case, the display unit 351 may continuously maintain the non-activated state. That is, the function related to health may be executed while maintaining the non-activated state of the display unit 351.

Meanwhile, if the blood pressure check mode is executed, blood pressure measurement is performed. If the blood pressure measurement is completed, a feedback may be output. As an example of the feedback, vibration may be generated in the main body, or sound notification or the like may be output. As the example, the band unit may be loosened, or the main body or band unit may not be contacted with the wrist.

If the blood pressure check mode is executed, blood pressure measurement is performed. If the blood pressure measurement is completed, a result value may be output on the display unit 351. In this case, the blood pressure measurement may be performed in the state in which the display unit 351 is non-activated. If the blood pressure measurement is completed, the result value may be output while the display unit 351 is being activated. As another example, a progress bar for notifying a procedure in which the blood pressure measurement is performed may be displayed on the display unit 351. If the blood pressure measurement is completed, a result value may be output.

The output of the result value may be performed only when the blood pressure is out of a predetermined range. That is, when the blood pressure is not a normal numerical value, the result value may be output while the display unit 351 is being activated in order to notify that the blood pressure is abnormal.

As another example, the result value may be always output, and a separate feedback may be provided when the blood pressure is not the normal numerical value as the measurement result. As a specific example, the controller may output sound notification, or may control the band unit to repeatedly tighten the wrist.

When the measured blood pressure is a dangerous numerical value, a result value may be output while the display unit 351 is being activated. In addition, treatment guidance information in which methods for recovering the blood pressure are listed may be displayed.

Figure 12:
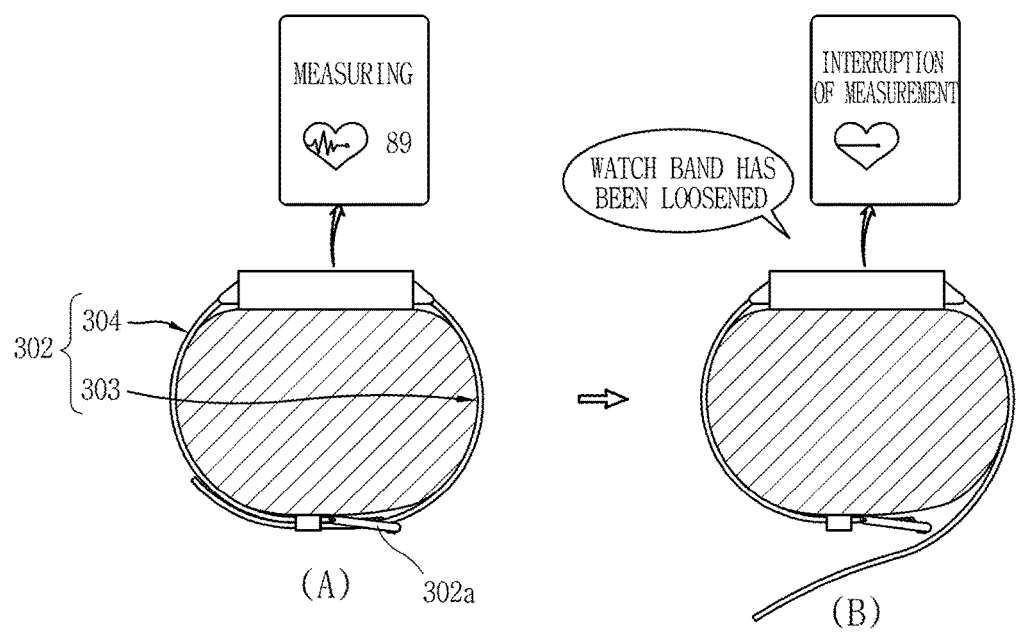
FIGS. 12 and 13 are conceptual diagrams illustrating control methods based on fastening of the band unit.
Figure 13:
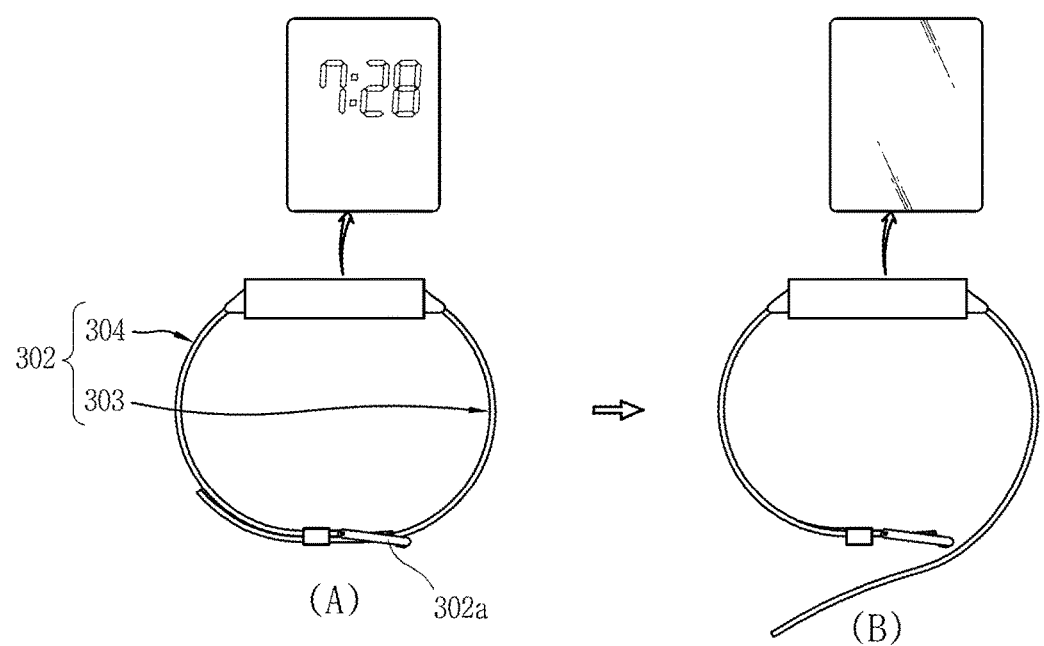

Next, embodiments in which control processing is changed depending on fastening of the band unit will be described in detail with reference to the accompanying drawings. FIGS. 12 and 13 are conceptual diagrams illustrating control methods based on fastening of the band unit.

Referring to these figures, the controller processes different control commands based on when a user input is applied in a state in which the first and second bands 303 and 304 are fastened to each other and when a user input is applied in a state in which the fastening between the first and second bands 303 and 304 is released. To this end, the terminal is formed to sense the state in which the first and second bands 303 and 304 are fastened to each other and the state in which the fastening between the first and second bands 303 and 304 is released. If the fastening between the first and second bands 303 and 304 is released, the controller may stop a function being executed in the state in which the first and second bands 303 and 304 are fastened to each other.

If the fastening between the first and second bands 303 and 304 is released while a specific function is being executed, the controller may stop the specific function.

As an example, if the fastening between the first and second bands 303 and 304 is released, the controller may switch the state of the terminal to a locking state.

As another example, if a blood pressure check mode is executed in the state in which the first and second bands 303 and 304 are fastened to each other, and the fastening between the first and second bands 303 and 304 is released while a living-body recognition sensor is being operated, the living-body recognition sensor is stopped so that blood pressure measurement is stopped.

If the fastening between the first and second bands 303 and 304 is released, notification information for notifying that the performance of the specific function is impossible may be output.

As shown in FIG. 13, if the fastening between the first and second bands 303 and 304 is released in a state in which the band unit is not contacted with skin, but the sensing unit is activated, and a specific function is being performed, the performance of the specific function is stopped. More specifically, a watch function is performed in a state in which the band unit is not contacted with skin, but the first and second bands 303 and 304 are fastened to each other. If the fastening between the first and second bands 303 and 304 is released, the operation of the watch function is stopped so that the display unit is non-activated. That is, if the fastening between the first and second bands 303 and 304 is released while the watch function is being performed as described in the exemplary embodiment of FIG. 13 in the state in which it is decided that the watch type mobile terminal is not worn, the performance of the watch function is stopped.

As described above, in the present disclosure, as it is set to apply an input to the watch type mobile terminal using the band unit, new user convenience can be provided. As the band unit is divided into areas for receiving different control commands, various input methods can be implemented.

Further, in the present disclosure, a locking release function is performed based on an operation pattern formed by a plurality of taps applied to the band unit. In this state, a locking state is released only when the operation pattern formed by sequentially connecting tap points of the sensed taps is matched to a predetermined operation pattern, and hence the user can release the locking state using a simple method of tapping an object. Accordingly, new user convenience can be provided.

Further, in the present disclosure, as a portion at which the bands are overlapped with each other is used as an input area, an input method when the watch type mobile terminal is worn may be different from that when the watch type mobile terminal is not worn. In addition, it is possible to implement a user input unit of a hybrid type, in which both touch key and physical key inputs are possible at a portion where the bands are overlapped (or fastened) with each other.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A watch type mobile terminal, comprising:
a main body including a display;
a band connected to the main body and configured to surround a user's wrist for wearing the mobile terminal on the wrist and comprising a first band and a second band respectively connected to both sides of the main body,
wherein the band is divided into a plurality of areas by fastening between the first band and the second band,
wherein the plurality of areas comprise a first area formed in the first band, a second area formed in the second band and a third area corresponding to an overlapped area in which the first and second bands are overlapped with each other;
a plurality of sensors provided on the band, the plurality of sensors configured to sense at least one tap applied to at least one of the first area, the second area or the third area comprised in the band;
an electric active polymer material contained in the band; and
a controller configured to:
detect, while the display is in a non-activated state, a predetermined pattern in which the at least one tap is applied, and to perform a function related to health,
wherein the predetermined pattern is defined by positions at which a plurality of the taps are respectively applied on the first area, the second area or the third area, and an order in which the plurality of taps are applied at the positions,
the function related to health based on the predetermined pattern while the non-activated state of the display is maintained, and
control the band to tighten on the wrist when the function related to health is executed, wherein power is supplied to the electric active polymer to tighten on the wrist based on the execution of the function related to health.

2. The watch type mobile terminal of claim 1, wherein the band includes the first band connected to a first side of the main body and the second band connected to a second side of the main body, the first and second bands configured to be fastened to each other, and
wherein, when the at least one tap that forms the predetermined pattern are applied while the first and second bands are fastened to each other, the controller performs the function corresponding to the predetermined pattern.

3. The watch type mobile terminal of claim 2, wherein the function being performed while the first and second bands are fastened to each other is stopped when the first and second bands are unfastened from each other.

4. The watch type mobile terminal of claim 1, wherein, when a number of touch points included in a first tap applied to the at least one the first area, the second area and the third area is different from a number of touch points included in a second tap applied to the at least one the first area, the second area and the third area, the controller recognizes the first and second taps as corresponding to different predetermined patterns.

5. A watch type mobile terminal, comprising:
a main body including a touch screen;
a band connected to the main body and configured to surround a user's wrist for wearing the mobile terminal on the wrist;
wherein the band comprises a first band and a second band respectively connected to both sides of the main body,
wherein the band is divided into a plurality of areas by fastening between the first band and the second band,
wherein the plurality of areas comprise a first area formed in the first band, a second area formed in the second band and a third area corresponding to an overlapped area in which the first and second bands are overlapped with each other, and
wherein a user's request corresponds to a predetermined pattern in which a plurality of taps are applied to at least one of the first area, the second area or the third area comprised in the band,
wherein the pattern is defined by touch positions at which the plurality of the taps are respectively applied on the first area, the second area, or the third area, and an order in which the plurality of taps are applied at the touch positions,
an electric active polymer material contained in the band;
a controller configured to:
receive the user's request received while a display of the touch screen is in a non-activated state;
execute a function related to health based on a user's request while the non-activated state of the display of the touch screen is maintained;
control the band to tighten on the wrist when the function related to health is executed,
wherein power is supplied to the electric active polymer to tighten on the wrist based on the execution of the function related to health.

6. The watch type mobile terminal of claim 5, wherein the function related to the health is an exercise function or a blood pressure check function.

7. The watch type mobile terminal of claim 6, wherein if the blood pressure check function is executed, blood pressure measurement is performed, and wherein if the blood pressure measurement is completed, a result value is output on the display of the touch screen.

8. The watch type mobile terminal of claim 5, wherein the function related to health is an exercise function, and
wherein if the exercise function is executed, an operation of recording exercise information is performed.

9. The watch type mobile terminal of claim 5, wherein the function related to health is a blood pressure check mode, and wherein if the fastening between the first and second bands is released, the blood pressure measurement is stopped.

10. A method of controlling a watch type mobile terminal comprising
a main body including a touch screen,
a band connected to the main body and configured to surround a user's wrist for wearing the mobile terminal on the wrist,
wherein the band comprises a first band and a second band respectively connected to both sides of the main body,
wherein the band is divided into a plurality of areas by fastening between the first band and the second band, wherein the plurality of areas comprise a first area formed in the first band, a second area formed in the second band and a third area corresponding to an overlapped area in which the first and second bands are overlapped with each other; and wherein a user's request corresponds to a predetermined pattern in which a plurality of taps are applied to at least one of the first area, the second area or the third area comprised in the band, wherein the predetermined pattern is defined by touch positions at which the plurality of the taps are respectively applied on the first area, the second area or the third area, and an order in which the plurality of taps are applied at the positions;

an electric active polymer material contained in the band, and a controller, the method comprising:

receiving the user's request received while a display of the touch screen is in a non-activated state;

executing, via the controller, a function related to health based on the user's request while the non-activated state of the display of the touch screen is maintained; and controlling, via the controller, the band to tighten on the wrist when the function related to health is executed, wherein power is supplied to the electric active polymer to tighten on the wrist based on the execution of the function related to heath.

11. The method of claim 10, wherein the function related to health is an exercise function or a blood pressure check function.

12. The method of claim 11, wherein if the blood pressure check function is executed, blood pressure measurement is performed, and wherein if the blood pressure measurement is completed, a result value is output on touch screen.

13. The method of claim 10, wherein the function related to health is an exercise function, and wherein if the exercise function is executed, an operation of recording exercise information is performed.

14. The method of claim 10, wherein the function related to health is a blood pressure check mode, and wherein if the fastening between the first and second bands is released, the blood pressure measurement is stopped.

* * * * *